United States Patent
Harvey et al.

(10) Patent No.: US 9,790,274 B2
(45) Date of Patent: Oct. 17, 2017

(54) MONOCLONAL ANTIBODIES TARGETING EPCAM FOR DETECTION OF PROSTATE CANCER LYMPH NODE METASTASES

(71) Applicant: THE BOARD OF REGENTS OF THE UNIVERSITY OF TEXAS SYSTEM, Austin, TX (US)

(72) Inventors: Barrett R. Harvey, Houston, TX (US); Kenneth L. Pinkston, Houston, TX (US); Ali Azhdarina, Houston, TX (US); Eva M. Sevick-Muraca, Houston, TX (US)

(73) Assignee: THE BOARD OF REGENTS OF THE UNIVERSITY OF TEXAS SYSTEM, Austin, TX (US)

(*) Notice: Subject to any disclaimer, the term of this patent is extended or adjusted under 35 U.S.C. 154(b) by 0 days.

(21) Appl. No.: 14/774,795

(22) PCT Filed: Mar. 12, 2014

(86) PCT No.: PCT/US2014/024021
§ 371 (c)(1),
(2) Date: Sep. 11, 2015

(87) PCT Pub. No.: WO2014/159531
PCT Pub. Date: Oct. 2, 2014

(65) Prior Publication Data
US 2016/0024207 A1     Jan. 28, 2016

Related U.S. Application Data

(60) Provisional application No. 61/782,601, filed on Mar. 14, 2013.

(51) Int. Cl.
C07K 16/00      (2006.01)
C07K 16/28      (2006.01)
C07K 16/30      (2006.01)
A61K 47/48      (2006.01)
A61K 51/10      (2006.01)
G01N 33/574     (2006.01)

(52) U.S. Cl.
CPC ........ *C07K 16/28* (2013.01); *A61K 47/48384* (2013.01); *A61K 47/48623* (2013.01); *A61K 51/1066* (2013.01); *A61K 51/1093* (2013.01); *C07K 16/30* (2013.01); *C07K 16/3053* (2013.01); *G01N 33/57434* (2013.01); *C07K 2317/33* (2013.01); *C07K 2317/55* (2013.01); *C07K 2317/622* (2013.01); *C07K 2317/76* (2013.01); *C07K 2317/92* (2013.01); *C07K 2317/94* (2013.01); *G01N 2333/705* (2013.01)

(58) Field of Classification Search
None
See application file for complete search history.

(56) References Cited

U.S. PATENT DOCUMENTS

2007/0081993 A1* 4/2007 Kufer ................. C07K 16/2809
                                                       424/144.1
2009/0169547 A1  7/2009 Sahin et al.

OTHER PUBLICATIONS

Hall et al, J Nucl Med 53:1-11, published Aug. 7, 2002.*
Hall et al, J of Nucelar Medicine, 53:1427-37, online published Aug. 2012, filed on Sep. 12, 2016.*
Hall et al., "Comparison of mAbs targeting epithelial cell adhesion molecule for the detection of prostate cancer lymph node metastases with multimodal contract agents: quantitative small-animal PET/CT and NIRF", *J Nucl Med.*, 53: 1427-1437, 2012.
International Preliminary Report on Patentability issued in International Application No. PCT/US2014/024021, dated Sep. 24, 2015.
International Search Report and Written Opinion issued in International Application No. PCT/US2014/024021, dated Jun. 16, 2014.
Mukherjee et al., "Identification of EpCAM as a molecular target of prostate cancer stroma", *British Journal of Cancer*, 97: 315-321, 2007.
Ruf et al., "Characterization of the new EpCAM-specific antibody HO-3: implications for trifunctional antibody immunotherapy of cancer", *British Journal of Cancer*, 97: 315-321, 2007.
Went et al., "Expression and prognostic significance of EpCAM", *J. Cancer Mol.*, 3(6): 169-174, 2008.

* cited by examiner

*Primary Examiner* — Lei Yao
(74) *Attorney, Agent, or Firm* — Parker Highlander PLLC

(57) ABSTRACT

Embodiments of the invention provide high affinity recombinant EpCAM-binding antibodies. Methods of using a such antibodies as imaging agents, diagnostics and therapeutics are also provided. Dual-nuclear and fluorescently labeled or singly fluorescently labeled contrast agents promise the advantage of molecularly-guided surgical resection via surgical field near-infrared fluorescence (NIRF) imaging following (in the case of dual labeled agents) nuclear imaging for general localization. Currently, nodal staging of most cancers is performed following lymph node (LN) biopsy and dissection for subsequent pathological examination.

14 Claims, 12 Drawing Sheets

*FIG. 11*

```
                       SEQUENCE LISTING

<160> NUMBER OF SEQ ID NOS: 16

<210> SEQ ID NO 1
<211> LENGTH: 5
<212> TYPE: PRT
<213> ORGANISM: Artificial sequence
<220> FEATURE:
<223> OTHER INFORMATION: Synthetic monoclonal antibody fragment

<400> SEQUENCE: 1

Ser Tyr Trp Ile Asn
1               5

<210> SEQ ID NO 2
<211> LENGTH: 18
<212> TYPE: PRT
<213> ORGANISM: Artificial sequence
<220> FEATURE:
<223> OTHER INFORMATION: Synthetic monoclonal antibody fragment

<400> SEQUENCE: 2

Gly Asp Ile Tyr Pro Gly Ser Gly Asn Ser His Tyr Asn Glu Lys Phe
1               5                   10                  15

Lys Ser

<210> SEQ ID NO 3
<211> LENGTH: 12
<212> TYPE: PRT
<213> ORGANISM: Artificial sequence
<220> FEATURE:
<223> OTHER INFORMATION: Synthetic monoclonal antibody fragment

<400> SEQUENCE: 3

Asn Tyr Tyr Gly Ser Ser Pro Phe Pro Met Asp Tyr
1               5                   10
```

```
<210> SEQ ID NO 4
<211> LENGTH: 17
<212> TYPE: PRT
<213> ORGANISM: Artificial sequence
<220> FEATURE:
<223> OTHER INFORMATION: Synthetic monoclonal antibody fragment

<400> SEQUENCE: 4

Lys Ser Ser Gln Ser Leu Leu Asn Ser Gly Asn Gln Lys Asn Tyr Leu
1               5                   10                  15

Thr

<210> SEQ ID NO 5
<211> LENGTH: 7
<212> TYPE: PRT
<213> ORGANISM: Artificial sequence
<220> FEATURE:
<223> OTHER INFORMATION: Synthetic monoclonal antibody fragment

<400> SEQUENCE: 5

Trp Ala Ser Thr Arg Glu Ser
1               5

<210> SEQ ID NO 6
<211> LENGTH: 9
<212> TYPE: PRT
<213> ORGANISM: Artificial sequence
<220> FEATURE:
<223> OTHER INFORMATION: Synthetic monoclonal antibody fragment

<400> SEQUENCE: 6

Gln Asn Asp Tyr Thr Tyr Pro Leu Thr
1               5

<210> SEQ ID NO 7
<211> LENGTH: 121
<212> TYPE: PRT
<213> ORGANISM: Artificial sequence
<220> FEATURE:
<223> OTHER INFORMATION: Synthetic monoclonal antibody fragment

<400> SEQUENCE: 7

Gln Val Gln Leu Gln Gln Ser Gly Ala Glu Leu Val Lys Pro Gly Thr
1               5                   10                  15

Ser Val Lys Leu Ser Cys Lys Ala Ser Gly Tyr Asn Phe Thr Ser Tyr
            20                  25                  30

Trp Ile Asn Trp Val Lys Leu Arg Pro Gly Gln Gly Leu Glu Trp Ile
        35                  40                  45

Gly Asp Ile Tyr Pro Gly Ser Gly Asn Ser His Tyr Asn Glu Lys Phe
    50                  55                  60

Lys Ser Lys Ala Thr Leu Thr Val Asp Thr Ser Ser Thr Ala Tyr
65                  70                  75                  80

Met Gln Leu Ser Ser Leu Ala Ser Gly Asp Ser Ala Leu Tyr Tyr Cys
                85                  90                  95

Ala Arg Asn Tyr Tyr Gly Ser Ser Pro Phe Pro Met Asp Tyr Trp Gly
                100                 105                 110

Gln Gly Thr Ser Val Thr Val Ser Ser
            115                 120

<210> SEQ ID NO 8
<211> LENGTH: 113
<212> TYPE: PRT
<213> ORGANISM: Artificial sequence
```

<220> FEATURE:
<223> OTHER INFORMATION: Synthetic monoclonal antibody fragment

<400> SEQUENCE: 8

Asp Ile Val Met Thr Gln Ser Pro Ser Ser Leu Ile Val Thr Ala Gly
1               5                   10                  15

Glu Lys Val Thr Met Ser Cys Lys Ser Ser Gln Ser Leu Leu Asn Ser
            20                  25                  30

Gly Asn Gln Lys Asn Tyr Leu Thr Trp Tyr Gln Gln Lys Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Leu Asn Ser Ala Gln Ala Glu Asp Leu Ala Val Tyr Tyr Cys Gln Asn
                85                  90                  95

Asp Tyr Thr Tyr Pro Leu Thr Phe Gly Ala Gly Thr Lys Leu Glu Ile
            100                 105                 110

Lys

<210> SEQ ID NO 9
<211> LENGTH: 5
<212> TYPE: PRT
<213> ORGANISM: Artificial
<220> FEATURE:
<223> OTHER INFORMATION: Synthetic monoclonal antibody fragment

<400> SEQUENCE: 9

Gly Tyr Asn Met Asn
1               5

<210> SEQ ID NO 10
<211> LENGTH: 18
<212> TYPE: PRT
<213> ORGANISM: Artificial sequence
<220> FEATURE:
<223> OTHER INFORMATION: Synthetic monoclonal antibody fragment

<400> SEQUENCE: 10

Gly Asn Ile Asp Pro Tyr Asn Gly Gly Ser Gly Phe Asp Gln Lys Phe
1               5                   10                  15

Lys Gly

<210> SEQ ID NO 11
<211> LENGTH: 8
<212> TYPE: PRT
<213> ORGANISM: Artificial sequence
<220> FEATURE:
<223> OTHER INFORMATION: Synthetic monoclonal antibody fragment

<400> SEQUENCE: 11

Glu Tyr Gly Ser Asn Phe Asp Tyr
1               5

<210> SEQ ID NO 12
<211> LENGTH: 11
<212> TYPE: PRT
<213> ORGANISM: Artificial sequence
<220> FEATURE:
<223> OTHER INFORMATION: Synthetic monoclonal antibody fragment

```
<400> SEQUENCE: 12

Arg Ala Ser Gln Asp Ile Gly Thr Tyr Leu Asn
1               5                   10

<210> SEQ ID NO 13
<211> LENGTH: 7
<212> TYPE: PRT
<213> ORGANISM: Artificial sequence
<220> FEATURE:
<223> OTHER INFORMATION: Synthetic monoclonal antibody fragment

<400> SEQUENCE: 13

Tyr Thr Ser Arg Leu His Ser
1               5

<210> SEQ ID NO 14
<211> LENGTH: 9
<212> TYPE: PRT
<213> ORGANISM: Artificial sequence
<220> FEATURE:
<223> OTHER INFORMATION: Synthetic monoclonal antibody fragment

<400> SEQUENCE: 14

Gln Gln Gly Asn Thr Leu Pro Trp Thr
1               5

<210> SEQ ID NO 15
<211> LENGTH: 117
<212> TYPE: PRT
<213> ORGANISM: Artificial sequence
<220> FEATURE:
<223> OTHER INFORMATION: Synthetic monoclonal antibody fragment

<400> SEQUENCE: 15

Gln Val Gln Leu Gln Gln Ser Gly Pro Glu Leu Glu Lys Pro Gly Gly
1               5                   10                  15

Ser Val Lys Ile Ser Cys Lys Ala Ser Gly Tyr Ser Phe Thr Gly Tyr
            20                  25                  30

Asn Met Asn Trp Val Lys Gln Ser Asn Gly Lys Ser Leu Glu Trp Ile
        35                  40                  45

Gly Asn Ile Asp Pro Tyr Asn Gly Gly Ser Gly Phe Asp Gln Lys Phe
    50                  55                  60

Lys Gly Lys Ala Thr Leu Thr Val Asp Thr Ser Ser Ser Thr Ala Tyr
65                  70                  75                  80

Met His Leu Lys Ser Leu Thr Ser Glu Asp Ser Ala Val Tyr Tyr Cys
                85                  90                  95

Ala Arg Glu Tyr Gly Ser Asn Phe Asp Tyr Trp Gly Gln Gly Thr Thr
            100                 105                 110

Leu Thr Val Ser Ser
        115

<210> SEQ ID NO 16
<211> LENGTH: 107
<212> TYPE: PRT
<213> ORGANISM: Artificial sequence
<220> FEATURE:
<223> OTHER INFORMATION: Synthetic monoclonal antibody fragment
```

```
<400> SEQUENCE: 16

Asp Ile Gln Met Thr Gln Ser Thr Ser Ser Leu Ser Ala Ser Leu Gly
 1               5                  10                  15

Asp Arg Val Thr Ile Ser Cys Arg Ala Ser Gln Asp Ile Gly Thr Tyr
                20                  25                  30

Leu Asn Trp Tyr Gln Gln Ala Asp Gly Thr Phe Lys Leu Leu Ile
            35                  40                  45

Tyr Tyr Thr Ser Arg Leu His Ser Gly Ile Pro Ser Arg Phe Ser Gly
        50                  55                  60

Ser Gly Ser Gly Thr Asp Phe Ser Leu Thr Ile Ser Asn Leu Gly Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
            100                 105
```

MONOCLONAL ANTIBODIES TARGETING EPCAM FOR DETECTION OF PROSTATE CANCER LYMPH NODE METASTASES

This application is a national phase application under 35 U.S.C. §371 of International Application No. PCT/US2014/024021, filed Mar. 12, 2014, which claims the benefit of U.S. Provisional Patent Application No. 61/782,601, filed Mar. 14, 2013, the entirety of each of which is incorporated herein by reference.

The invention was made with government support under Grant No. U54 CA136404 awarded by the National Institutes of Health. The government has certain rights in the invention.

INCORPORATION OF SEQUENCE LISTING

The sequence listing that is contained in the file named "UTFHP0293WO_ST25.txt", which is 8 KB (as measured in Microsoft Windows®) and was created on Mar. 12, 2014, is filed herewith by electronic submission and is incorporated by reference herein.

BACKGROUND OF THE INVENTION

1. Field of the Invention

The present invention relates generally to the field of cancer biology. More particularly, it concerns monoclonal antibodies targeting EpCAM antigen.

2. Description of Related Art

Dual-nuclear and fluorescently labeled or singly fluorescently labeled contrast agents promise the advantage of molecularly-guided surgical resection via surgical field near-infrared fluorescence (NIRF) imaging following (in the case of dual labeled agents) nuclear imaging for general localization. Currently, nodal staging of most cancers is performed following lymph node (LN) biopsy and dissection for subsequent pathological examination. As in most cancers, imaging of LN involvement in prostate cancer (PCa) lacks sensitivity and specificity (Shukla-Dave et al., 2007) and as a result, (extended) pelvic LN dissection (PLND), which provides higher staging accuracy (Berney et al., 2011), is rapidly becoming the standard-of-care at the time of radical prostatectomy. Yet with early detection of PCa enabled by prostate-specific antigen (PSA) screening, a substantial and growing population of PCa patients may be overtreated (Daskivich et al., 2011) and encounter the resultant morbidity of lower extremity lymphedema (Pilepich et al, 1984; Musch et al., 2008; Cormier et al., 2010). A multimodal contrast agent is needed to provide accurate, non-invasive LN staging of PCa and to guide surgical resection of cancer-positive LNs, while sparing resection of cancer-negative LNs and potentially reducing surgical morbidity and improving survivorship.

In addition, surgical resection of epithelial cancers in body areas with critical areas, such as retroperitoneal or head and neck cancers require resection of tissues with clear margins free of cancer. Cancer positive margins, detected in surgical pathology from resected tissues, require surgeons to excise additional tissues, often times involving critical structures which compromise quality of life. Yet there is no indication within the field of surgical view, which structures are cancer positive and which are not. Because cancer survivorship critically depends upon reducing residual tumor burden by removal ALL cancerous tissues, it is critical that there is a means to direct surgical resection of cancerous tissues while sparing normal tissues, that may involve critical body structures.

SUMMARY OF THE INVENTION

The present invention provides methods and compositions for use in detecting and monitoring epithelial cancer cells. In some aspects, methods and compositions of the embodiments can be used for monitoring the spread of a epithelial cancer from primary tumor sites to the lymphatics and/or for identifying cancer-positive lymph nodes, or for delineating within the surgical field of view, cancer versus cancer free tissues.

In some embodiments, the present invention is directed towards an isolated or recombinant monoclonal antibody that specifically binds to a EpCAM polypeptide (e.g., a human EpCAM polypeptide). In certain aspects, an antibody competes for the binding of an EpCAM polypeptide with the "153" or "7" monoclonal antibody. In further aspects, an antibody of the embodiments can be defined as having an equilibrium $K_D$ relative to a human EpCAM polypeptide of less than about 5 nM or 10 nM, e.g., an equilibrium $K_D$ of between about 0.1 and 10 nM. In certain aspects, the antibody can comprise all or part of the heavy chain variable region and/or the light chain variable region of EpCAM-binding monoclonal antibodies. In a further aspect, a polypeptide can comprise an amino acid sequence that corresponds to a first, second, and/or third complementarity determining region (CDR) from the light variable and/or heavy variable chain of a EpCAM monoclonal antibody of the present invention.

Thus, in certain aspects, an isolated antibody comprises CDR sequences at least 80%, 90% or 95% identical to the CDR regions of the "153" or "7" antibody heavy and light chain amino acid sequences. In further aspects, an antibody comprises CDR regions identical to the 153 or 7, except for one or two amino acid substitutions, deletions or insertions at one or more of the CDRs. For example, the antibody can comprise CDRs wherein the CDR sequences comprise 1 or 2 amino acid substitutions in the $V_H$ CDR1, $V_H$ CDR2, $V_H$ CDR3, $V_L$ CDR1, $V_L$ CDR2 and/or $V_L$ CDR3 relative to the CDRs of a 153 or 7 monoclonal antibody. Thus, in some specific aspects, an antibody of the embodiments comprises (a) a first $V_H$ CDR at least 80% identical to $V_H$ CDR1 of 153 (SEQ ID NO: 1), or 7 (SEQ ID NO: 9); (b) a second $V_H$ CDR at least 80% identical to $V_H$ CDR2 of 153 (SEQ ID NO: 2), or 7 (SEQ ID NO: 10); (c) a third $V_H$ CDR at least 80% identical to $V_H$ CDR3 of 153 (SEQ ID NO: 3), or 7 (SEQ ID NO: 11); (d) a first $V_L$ CDR at least 80% identical to $V_L$ CDR1 of 153 (SEQ ID NO: 4), or 7 (SEQ ID NO: 12); (e) a second $V_L$ CDR at least 80% identical to $V_L$ CDR2 of 153 (SEQ ID NO: 5), or 7 (SEQ ID NO: 13); and (f) a third $V_L$ CDR at least 80% identical to $V_L$ CDR3 of 153 (SEQ ID NO: 6), or 7 (SEQ ID NO: 14).

In certain aspects, an antibody of the embodiments comprises each of the CDRs of a 153 antibody, such as, (a) a first $V_H$ CDR is identical to SEQ ID NO: 1; (b) a second $V_H$ CDR is identical to SEQ ID NO: 2; (c) a third $V_H$ CDR is identical to SEQ ID NO: 3; (d) a first $V_L$ CDR is identical to SEQ ID NO: 4; (e) a second $V_L$ CDR is identical to SEQ ID NO: 5; and (f) a third $V_L$ CDR is identical to SEQ ID NO: 6. Thus, in further aspects, the isolated antibody comprises a $V_H$ domain at least about 80% identical to the $V_H$ domain of 153 (SEQ ID NO: 7) and a $V_L$ domain at least about 80% identical to the $V_L$ domain of 153 (SEQ ID NO: 8). In some aspects, the isolated antibody comprises $V_H$ and $V_L$ domains identical to or derived from those of monoclonal antibody 153.

In certain aspects, an antibody of the embodiments comprises each of the CDRs of a 7 antibody, such as, (a) a first $V_H$ CDR is identical to SEQ ID NO: 9; (b) a second $V_H$ CDR is identical to SEQ ID NO: 10; (c) a third $V_H$ CDR is identical to SEQ ID NO: 11; (d) a first $V_L$ CDR is identical to SEQ ID NO: 12; (e) a second $V_L$ CDR is identical to SEQ ID NO: 13; and (f) a third $V_L$ CDR is identical to SEQ ID NO: 14. Thus, in further aspects, the isolated antibody comprises a $V_H$ domain at least about 80% identical to the $V_H$ domain of 7 (SEQ ID NO: 15) and a $V_L$ domain at least about 80% identical to the $V_L$ domain of 7 (SEQ ID NO: 16). In some aspects, the isolated antibody comprises $V_H$ and $V_L$ domains identical to or derived from those of monoclonal antibody 7.

In some aspects, an antibody of the embodiments may be an IgG (e.g., IgG1, IgG2, IgG3 or IgG4), IgM, IgA, or an antigen binding fragment thereof. The antibody may be a Fab', a F(ab')2 a F(ab')3, a monovalent scFv, a bivalent scFv, or a single domain antibody. The antibody may be a human, humanized, or de-immunized antibody. In a further aspect, the isolated antibody is the "153" or "7" monoclonal antibody and products derived thereof.

In some aspects, an antibody may be conjugated to an imaging agent or a therapeutic agent. For example, the therapeutic agent can be a chemotherapeutic agent, a toxin, or a radionuclide (e.g., a radionuclide sequestered by a chelate). Imagining agents for use according to the embodiments include, without limitation, fluorophores, dyes, a MRI active agent, radionuclides or a fluorescence radionuclide. In certain aspects, an antibody can be conjugated to two or more agents, such as to a fluorophore and a radio-imaging agent.

In another embodiment, there is provided a recombinant polypeptide comprising an antibody $V_H$ domain comprising CDRs 1-3 of the $V_H$ domain of 153 (SEQ ID NOs: 1, 2 and 3); or CDRs 1-3 of the $V_H$ domain of 7 (SEQ ID NOs: 9, 10 and 11). In another embodiment a recombinant polypeptide is provided comprising an antibody $V_L$ domain comprising CDRs 1-3 of the $V_L$ domain of 153 (SEQ ID NOs: 4, 5 and 6); or 7 (SEQ ID NOs: 12, 13 and 14).

In some embodiments, there is provided an isolated polynucleotide molecule comprising nucleic acid sequence encoding an antibody or a polypeptide comprising an antibody $V_H$ or $V_L$ domain disclosed herein. In some aspects, the polynucleotide molecule is an expression vector.

In further embodiments, a host cell is provided that produces a monoclonal antibody or recombinant polypeptide of the embodiments. In some aspects, the host cell is a mammalian cell, a yeast cell, a bacterial cell, a ciliate cell, or an insect cell. In certain aspects, the host cell is a hybridoma cell.

In still further embodiments, there is provided a method of manufacturing an antibody of the present embodiments comprising expressing one or more polynucleotide molecule(s) encoding a $V_L$ or $V_H$ chain of an antibody disclosed herein in a cell and purifying the antibody from the cell.

In additional embodiments, pharmaceutical compositions are provided comprising an antibody or antibody fragment disclosed supra. Such a composition may further comprise a pharmaceutically acceptable carrier and may or may not contain additional active ingredients.

In yet further aspects, a polypeptide of the embodiments comprises an amino acid segment that is at least 80, 85, 90, 95, 96, 97, 98, 99, or 100% identical (or any range derivable therein) to a V, VJ, VDJ, D, DJ, J or CDR domain of a EpCAM-binding antibody (as provided in Table 1). For example, a polypeptide may comprise 1, 2 or 3 amino acid segment that are at least 80, 85, 90, 95, 96, 97, 98, 99, or 100% identical (or any range derivable therein) to CDRs 1, 2, and/or 3 a EpCAM-binding antibody as provided in Table 1.

In still a further embodiment there is provided a method of preparing a subject for imaging, comprising administering to the subject an effective amount of an antibody of the embodiments, wherein the antibody is conjugated to an imaging agent. In a related embodiment a method is provided for imaging a subject comprising (a) administering an effective amount of an antibody of the embodiments to the subject, wherein the antibody is conjugated to an imaging agent; and (b) detecting the imaging agent in the subject. Depending on the imaging agent or agents used, detecting the imaging agent, can comprises performing fluorescence imaging, PET, MRI, CT, SPECT or a combination thereof on the subject. For example, in the case of NIR fluorescence imaging, images can be acquired using a fluorescence imaging system as described in U.S. Pat. Nos. 7,328,059 and 8,084,753 and U.S. Patent Publications US20080064954, US20100305453, US20110071403, US20110280811, as well as in Sevick-Muraca 2012 (Translation of near-infrared fluorescence imaging technologies: emerging clinical applications. *Annu. Rev. Med.* 63, 217-231), each of which is incorporated herein by reference. In a further aspect, the imaging agent can be a fluorophore, a dye, an MRI contrast agent or a radionuclide. In certain aspects, a subject for imaging is a subject having as cancer. Accordingly, in aspects, imaging a subject comprises imaging cancer cells in a subject. For example, a method can be defined as a method for detecting cancer metastasis, such as lymphoid metastasis (e.g., lymph node metastasis of a prostate cancer) or for delineating tumor margins and infiltrating cancer within the surgical field of view.

In another embodiment, there is provided a method for detecting a cancer in a subject comprising testing for the presence of elevated EpCAM relative to a control in a sample from the subject, wherein the testing comprises contacting the sample with an antibody disclosed herein. For example, the method may be an in vitro or in vivo method. Examples, of methods that can be used to test a sample for EpCAM expression include, without limitation, ELISA, immunohistochemistry (IHC), fluorescence microscopy, and flow cytometry.

In embodiments of the present invention, there is provided a method for treating a subject having a cancer comprising administering an effective amount of an antibody disclosed herein. In certain aspects, the antibody is a monoclonal antibody of the present invention, such as 153 or 7 monoclonal antibody, or a recombinant polypeptide comprising antibody segments derived therefrom. In some aspects, the antibody is conjugated to a therapeutic agent, such as a toxin or chemotherapeutic agent. A method may further comprise administering at least a second anticancer therapy to the subject. Examples of the second anticancer therapy include, but are not limited to, surgical therapy, chemotherapy, radiation therapy, cryotherapy, hormonal therapy, immunotherapy, or cytokine therapy. Such a second therapy can be administered before, after or essentially simultaneously with an antibody therapeutic of the embodiments. In further aspects, the method may further comprise administering a composition of the present embodiments more than one time to the subject, such as, for example, 1, 2, 3, 4, 5, 6, 7, 8, 9, 10, 15, 20 or more times.

In certain aspects, a cancer, as described herein, may be a breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer, skin cancer, or other epithelial cancer. In one aspect, the cancer is an EpCAM positive cancer, such as a positive prostate cancer.

Antibody, therapeutics and imaging agents detailed herein may be administered systemically, locally or distally. In some aspects, an antibody may be administered intravenously, intradermally, intratumorally, intramuscularly, intraperitoneally or subcutaneously.

As used herein the specification, "a" or "an" may mean one or more. As used herein in the claim(s), when used in conjunction with the word "comprising", the words "a" or "an" may mean one or more than one.

The use of the term "or" in the claims is used to mean "and/or" unless explicitly indicated to refer to alternatives only or the alternatives are mutually exclusive, although the disclosure supports a definition that refers to only alternatives and "and/or." As used herein "another" may mean at least a second or more.

Throughout this application, the term "about" is used to indicate that a value includes the inherent variation of error for the device, the method being employed to determine the value, or the variation that exists among the study subjects.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 7A demonstrates binding specificity of mAb 153 to human MCF7 cells, as shown by the increase in MFI for the cell population incubated with mAb 153 (right-most peak) relative to the MFI for cells incubated with only PE-labeled secondary antibody (left-most peak), while binding of mAb 153 to mouse cells was not detectable (FIG. 7C), as shown by an MFI that was indistinguishable from that of the mouse cells incubated with only PE-labeled secondary antibody. FIGS. 7B and D demonstrate binding specificity of mAb G8.8 to mouse 4T1 cells and no detectable binding to the human cells. Additionally, the entire generated panel of anti-EpCAM mAbs were tested against 4T1 cells and, like mAb 153, demonstrated no detectable binding.

FIG. 11. Affinity maturation of lead antibody candidates using APEx directed evolution.

DESCRIPTION OF ILLUSTRATIVE EMBODIMENTS

Figure 1:
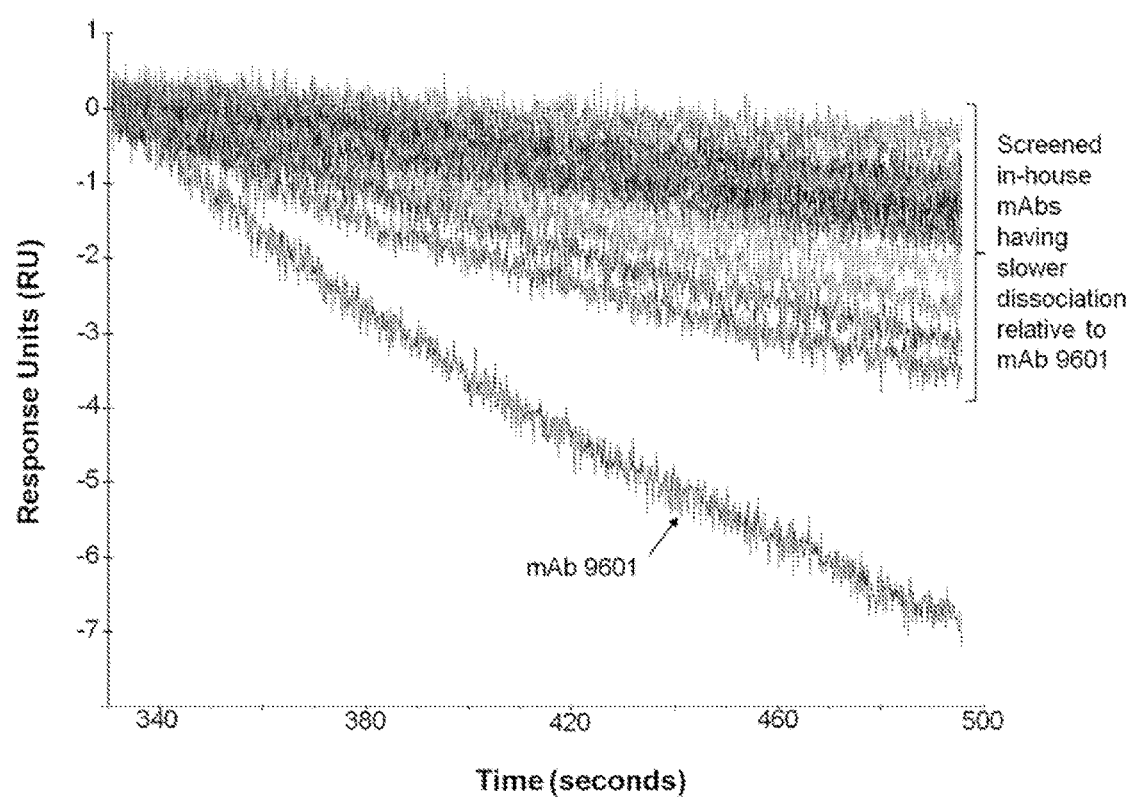
FIG. 1. Dissociation analysis of mAbs from EpCAM/Fc by surface plasmon resonance (SPR) analysis. In series, the in-house panel of mAbs and commercial mAb 9601, were captured on a CM5 Sensor chip coupled with goat anti-mouse followed by EpCAM/Fc analyte. Dissociation of EpCAM/Fc from mAb is monitored as a decrease in response units (RU) over time.

Epithelial cell adhesion molecule (EpCAM) is overexpressed in many metastasizing epithelial cancers (Spizzo et al., 2006; Spizzo et al., 2004; Went et al., 2006; Fong et al., 2008; Baeuerle et al., 2007) and is an ideal target for dual-labeled agent development. Expression of EpCAM in prostatic biopsy samples has been shown through immunohistochemistry (IHC) to be elevated with biochemical recurrence (Benko et al., 2011) and correlated with Gleason score (Benko et al., 2011; Mukherjee et al., 2009), which is an important prognostic factor and is now incorporated into PCa staging nomograms (Edge et al., 2010). In over 441 human PCa tissue samples, microarray analyses showed that 80%-100% of all prostatic intraepithelial neoplasia, localized PCa, hormone-refractory local recurrences, and lymph node (LN) metastases overexpressed EpCAM, suggesting it as an excellent diagnostic imaging marker for PCa LN staging (Zellweger et al., 2005).

Previously, the inventors developed a dual-labeled anti-EpCAM monoclonal antibody (mAb) for multimodal diagnostic imaging in a preclinical model of metastatic PCa, but optimization of binding affinity and pharmacodynamics of antibody (Ab)-based agents is needed to maximize imaging sensitivity and specificity (Hall et al., 2011). While anti-EpCAM mAbs have been under investigation as therapeutics against epithelial cancers, development has been focused upon attenuating binding affinity to reduce systemic toxicity, and enhancing Ab-dependent cellular cytotoxicity (ADCC) and complement-dependent cytotoxicity (CDC) for therapeutic action. As a diagnostic, the design of anti-EpCAM mAb-based imaging agents requires enhanced affinity for improved specificity at sub-therapeutic dosages, elimination of pharmacologic action through ADCC and CDC, and reduced circulation times to improve target-to-background ratios.

Herein, the inventors developed and quantitatively compared a panel of mAbs specific for human EpCAM, from which high-affinity candidates with specificity for non-overlapping EpCAM epitopes were dual-labeled with a near-infrared (NIR) fluorophore and a conventional chelator/radiotracer, for subsequent assessment via NIRF imaging and quantitative PET/CT for in vivo detection of metastatic LNs in a DsRed-reporter gene mouse model of PCa LN metastasis. The inventors sought to first assess whether differences in binding affinity impacted quantitative imaging performance of whole mAb-based contrast agents assessed by receiver operating characteristic (ROC) curve analyses prior to engineering mAb fragment-based imaging agents that will lack properties of therapeutic ADCC and CDC but will have improved imaging pharmacokinetics. A commercially available anti-EpCAM mAb, which was dual-labeled and used in previous preclinical imaging (Hall et al., 2011), was also included in the ROC curve analyses for comparison and selection of candidate mAbs for further imaging agent optimization.

Two high-affinity candidate mAbs with specificity for non-overlapping epitopes on the EpCAM surface antigen were chosen for further evaluation in vivo. After conjugation with $^{64}$Cu and IRDye800 CW, dual-labeled specific or isotype control mAb was administered intravenously to male Nu/Nu mice at 10-12 weeks post-orthotopic implantation of DsRed-expressing PC3 cells. Within 18-24 hours, non-invasive µPET/CT was performed as well as in vivo and in situ DsRed reporter-gene and near-infrared fluorescence (NIRF) imaging to detect primary tumors and metastatic LNs. From quantitative analyses of non-invasive PET/CT images of LNs from the inventor's in vivo DsRed-reporter gene mouse model, the inventors demonstrated greater concordance between µPET/CT imaging and the DsRed fluorescence, cancer-positive indicator using two in-house generated mAbs relative to the commercial mAb tested. MAbs 7 and 153 performed with greater sensitivity during µPET/CT when compared to commercial mAb and yielded strong correlations between qualitative NIRF and DsRed-reporter gene imaging. Qualitative comparison of NIRF imaging demonstrated similar results to those found from DsRed reporter-gene imaging and µPET/CT. MAbs 7 and 153 are attractive candidates for further agent optimization aimed at enhancing sensitivity and specificity for detection of metastatic LNs in PCa and creating Ab fragments to reduce circulation times and eliminate Fc binding regions responsible for therapeutic action and nonspecific binding.

There is a clear surgical need for improvements in cancer and metastasis detection. Although EpCAM has been a putative cancer therapeutic target for decades, this is one of the first efforts to specifically engineer the detection agent for diagnostic use. This could be used as an intraoperative means for surgeons to identify and specifically remove cancer positive lymph nodes during prostatectomy surgery and subsequent lymphadectomy. Additionally, for CTC detection, with the Veridex FDA approved platform, a clear association has been made with CTC quantification and lifespan of patient, demonstrating value of this technology in determining direction of patient treatment (Wallwiener et al., 2013; Young et al., 2012; Sun et al., 2012). The next logical step is to improve the anti-EpCAM agent affinity as it is the primary means of CTC isolation. Improvements in affinity should translate into improved CTC detection while minimizing the blood sample volume necessary from the patient.

I. Definitions

As used herein, and unless otherwise indicated, the terms "treat," "treating," "treatment" and "therapy" contemplate an action that occurs while a patient is suffering from epitheilal cancers and related disorders that reduces the severity of one or more symptoms or effects of epitheilal cancers, metastisis or a related disease or disorder, such as but not limited to breast cancer, lung cancer, head & neck cancer, prostate cancer, esophageal cancer, tracheal cancer, brain cancer, liver cancer, bladder cancer, stomach cancer, pancreatic cancer, ovarian cancer, uterine cancer, cervical cancer, testicular cancer, colon cancer, rectal cancer, skin cancer, or other epithelial cancer and metastasis associated with such. In one aspect, the cancer is an EpCAM positive cancer, such as a positive prostate cancer.

Where the context allows, the terms "treat," "treating," and "treatment" also refers to actions taken toward ensuring that individuals at increased risk of epitheilal cancer-metastasis are able to receive appropriate surgical and/or other medical intervention prior to onset of epitheilal cancers and disorders. As used herein, and unless otherwise indicated, the terms "prevent," "preventing," and "prevention" contemplate an action that occurs before a patient begins to suffer from epitheilal cancers and related disorders that delays the onset of, and/or inhibits or reduces the severity of, epitheilal cancers and related disorders. As used herein, and unless otherwise indicated, the terms "manage," "managing," and "management" encompass preventing, delaying, or reducing the severity of a recurrence of epitheilal cancers, metastisis and related disorders in a patient who has already suffered from such a disease or condition. The terms encompass modulating the threshold, development, and/or duration of the epitheilal cancers, metastisis and related disorders or changing how a patient responds to the epitheilal cancers, metastisis and related disorders.

As used herein, and unless otherwise specified, a "therapeutically effective amount" of a compound is an amount sufficient to provide any therapeutic benefit in the treatment or management of epitheilal cancers, metastisis and related disorders or to delay or minimize one or more symptoms associated with epitheilal cancers, metastisis and related disorders. A therapeutically effective amount of a compound means an amount of the compound, alone or in combination with one or more other therapies and/or therapeutic agents, which provides any therapeutic benefit in the treatment or management of epitheilal cancers, metastisis and related disorders, or related diseases or disorders. The term "therapeutically effective amount" can encompass an amount that alleviates epitheilal cancers, metastisis and related disorders, improves or reduces epitheilal cancers, metastisis and related disorders, improves overall therapy, or enhances the therapeutic efficacy of another therapeutic agent. The "therapeutically effective amount" can be identified at an earlier stage with parameters of 1 epitheilal cancers, metastisis and related epitheilal cancers, metastisis and related function as identified herein.

As used herein, the term "lymphatic structure(s)" refers to all or a portion of structures that make up a mammalian lymphatic system including without limitation, lymph nodes, collecting vessels, lymph trunks, lymph ducts, capillaries, or combinations thereof. The architecture of the lymphatic structures can be described by tortuosity, density, dilation, and other parameters.

As used herein, the term "near-infrared" refers to electromagnetic radiation at wavelengths ranging from about 750 nm to about 900 nm.

As used herein, and unless otherwise specified, the term "functional imaging" of lymph structures refers to how the structures function in terms of update of dye, the lymphatic flow as determined by the dye, dynamics of flow, and direction of flow of lymph and the associated materials carried by it. The function of the lymphatic structures can be described by lymph velocity, period or frequency of propulsive events, permeability, and other parameters that provide evidence of dysfunction in comparison to normal function imaged in healthy control animals or human subjects. If lymph vessels are "functional" they transport materials, and imaging methods disclosed herein describe this.

II. EpCAM

EpCAM, a 40 kD type I transmembrane glycoprotein involved in cell-to-cell interactions and adhesion, is stably overexpressed by most types of epithelial cancers. EpCAM was the first identified tumor-associated antigen that today is known to be intensely and uniformly expressed on epithelial carcinomas while being less intensely expressed, sequestered, and less accessible on the basolateral cell surface of normal epithelia, making it a useful marker for diagnostic applications.

Proliferation of most carcinomas is associated with overexpression of epithelial cell adhesion molecule (EpCAM), a 40 kDa Type I transmembrane protein found on all epithelial cells yet absent on other cell types, including those in lymphoid tissue. Absence of EpCAM in normal lymphatics makes it an attractive marker for studying lymph node (LN) metastases of carcinomas to improve LN staging accuracy.

These monoclonal antibodies have demonstrated higher affinity and specificity compared to commercially available anti-EpCAM antibody 9601 (R&D Systems).

III. Diagnostic Antibodies

In certain embodiments, an antibody or a fragment thereof that binds to at least a portion of EpCAM protein and its associated use in diagnosis and imaging of diseases are contemplated. As used herein, the term "antibody" is intended to refer broadly to any immunologic binding agent, such as IgG, IgM, IgA, IgD, and IgE as well as polypeptides comprising antibody CDR domains that retain antigen binding activity. The antibody may be selected from the group consisting of a chimeric antibody, an affinity matured antibody, a polyclonal antibody, a monoclonal antibody, a humanized antibody, a human antibody, or an antigen-binding antibody fragment or a natural or synthetic ligand. Preferably, the anti-EpCAM antibody is a monoclonal antibody or a humanized antibody. By known means and as described herein, polyclonal or monoclonal antibodies, antibody fragments, and binding domains and CDRs (including engineered forms of any of the foregoing) may be created that are specific to EpCAM protein, one or more of its respective epitopes, or conjugates of any of the foregoing, whether such antigens or epitopes are isolated from natural sources or are synthetic derivatives or variants of the natural compounds.

Examples of antibody fragments suitable for the present invention include, without limitation: (i) the Fab fragment, consisting of VL, VH, CL, and CH1 domains; (ii) the "Fd" fragment consisting of the VH and CH1 domains; (iii) the "Fv" fragment consisting of the VL and VH domains of a single antibody; (iv) the "dAb" fragment, which consists of a VH domain; (v) isolated CDR regions; (vi) F(ab')2 fragments, a bivalent fragment comprising two linked Fab fragments; (vii) single chain Fv molecules ("scFv"), wherein a VH domain and a VL domain are linked by a peptide linker that allows the two domains to associate to form a binding domain; (viii) bi-specific single chain Fv dimers (see U.S. Pat. No. 5,091,513); and (ix) diabodies, multivalent or multispecific fragments constructed by gene fusion (US Patent App. Pub. 20050214860). Fv, scFv, or diabody molecules may be stabilized by the incorporation of disulphide bridges linking the VH and VL domains. Minibodies comprising a scFv joined to a CH3 domain may also be made (Hu et al., 1996).

Antibody-like binding peptidomimetics are also contemplated in embodiments. Liu et al. (2003) describe "antibody like binding peptidomimetics" (ABiPs), which are peptides that act as pared-down antibodies and have certain advantages of longer serum half-life as well as less cumbersome synthesis methods.

Animals may be inoculated with an antigen, such as purified peptide or cells expressing the antigen on their surface, in order to produce antibodies specific for EpCAM protein. Frequently an antigen is bound or conjugated to another molecule to enhance the immune response. As used herein, a conjugate is any peptide, polypeptide, protein, or non-proteinaceous substance bound to an antigen that is used to elicit an immune response in an animal. Antibodies produced in an animal in response to antigen inoculation comprise a variety of non-identical molecules (polyclonal antibodies) made from a variety of individual antibody producing B lymphocytes. A polyclonal antibody is a mixed population of antibody species, each of which may recognize a different epitope on the same antigen. Given the correct conditions for polyclonal antibody production in an animal, most of the antibodies in the animal's serum will recognize the collective epitopes on the antigenic compound to which the animal has been immunized. This specificity is further enhanced by affinity purification to select only those antibodies that recognize the antigen or epitope of interest.

A monoclonal antibody is a single species of antibody wherein every antibody molecule recognizes the same epitope because all antibody producing cells are derived from a single B-lymphocyte cell line. The methods for generating monoclonal antibodies (MAbs) generally begin along the same lines as those for preparing polyclonal antibodies. In some embodiments, rodents such as mice and rats are used in generating monoclonal antibodies. In some embodiments, rabbit, sheep, or frog cells are used in generating monoclonal antibodies. The use of rats is well known and may provide certain advantages. Mice (e.g., BALB/c mice) are routinely used and generally give a high percentage of stable fusions.

Hybridoma technology involves the fusion of a single B lymphocyte from a mouse previously immunized with a EpCAM antigen with an immortal myeloma cell (usually mouse myeloma). This technology provides a method to propagate a single antibody-producing cell for an indefinite number of generations, such that unlimited quantities of structurally identical antibodies having the same antigen or epitope specificity (monoclonal antibodies) may be produced.

In one embodiment, the antibody is a chimeric antibody, for example, an antibody comprising antigen binding sequences from a non-human donor grafted to a heterologous non-human, human, or humanized sequence (e.g., framework and/or constant domain sequences). Methods have been developed to replace light and heavy chain constant domains of the monoclonal antibody with analogous domains of human origin, leaving the variable regions of the foreign antibody intact. Alternatively, "fully human" monoclonal antibodies are produced in mice transgenic for human immunoglobulin genes. Methods have also been developed to convert variable domains of monoclonal antibodies to more human form by recombinantly constructing antibody variable domains having both rodent, for example, mouse, and human amino acid sequences. In "humanized" monoclonal antibodies, only the hypervariable CDR is derived from mouse monoclonal antibodies, and the framework and constant regions are derived from human amino acid sequences (see U.S. Pat. Nos. 5,091,513 and 6,881, 557). It is thought that replacing amino acid sequences in the antibody that are characteristic of rodents with amino acid sequences found in the corresponding position of human antibodies will reduce the likelihood of adverse immune reaction during therapeutic use. A hybridoma or other cell producing an antibody may also be subject to genetic mutation or other changes, which may or may not alter the binding specificity of antibodies produced by the hybridoma.

Methods for producing polyclonal antibodies in various animal species, as well as for producing monoclonal antibodies of various types, including humanized, chimeric, and fully human, are well known in the art and highly predictable. For example, the following U.S. patents and patent applications provide enabling descriptions of such methods: U.S. Patent Application Nos. 2004/0126828 and 2002/ 0172677; and U.S. Pat. Nos. 3,817,837; 3,850,752; 3,939, 350; 3,996,345; 4,196,265; 4,275,149; 4,277,437; 4,366, 241; 4,469,797; 4,472,509; 4,606,855; 4,703,003; 4,742, 159; 4,767,720; 4,816,567; 4,867,973; 4,938,948; 4,946, 778; 5,021,236; 5,164,296; 5,196,066; 5,223,409; 5,403, 484; 5,420,253; 5,565,332; 5,571,698; 5,627,052; 5,656, 434; 5,770,376; 5,789,208; 5,821,337; 5,844,091; 5,858, 657; 5,861,155; 5,871,907; 5,969,108; 6,054,297; 6,165, 464; 6,365,157; 6,406,867; 6,709,659; 6,709,873; 6,753, 407; 6,814,965; 6,849,259; 6,861,572; 6,875,434; and 6,891,024. All patents, patent application publications, and other publications cited herein and therein are hereby incorporated by reference in the present application.

Antibodies may be produced from any animal source, including birds and mammals. Preferably, the antibodies are ovine, murine (e.g., mouse and rat), rabbit, goat, guinea pig, camel, horse, or chicken. In addition, newer technology permits the development of and screening for human antibodies from human combinatorial antibody libraries. For example, bacteriophage antibody expression technology allows specific antibodies to be produced in the absence of animal immunization, as described in U.S. Pat. No. 6,946,546, which is incorporated herein by reference. These techniques are further described in: Marks (1992); Stemmer (1994); Gram et al. (1992); Barbas et al. (1994); and Schier et al. (1996).

It is fully expected that antibodies to EpCAM will have the ability to bind EpCAM regardless of the animal species, monoclonal cell line, or other source of the antibody. Certain animal species may be less preferable for generating diagnostic imaging antibodies because they may be more likely to cause allergic response due to activation of the complement system through the "Fc" portion of the antibody. However, whole antibodies may be enzymatically digested into "Fc" (complement binding) fragment, and into antibody fragments having the binding domain or CDR. Removal of the Fc portion reduces the likelihood that the antigen antibody fragment will elicit an undesirable immunological response, and thus, antibodies without Fc may be preferential for prophylactic or therapeutic treatments. As described above, antibodies may also be constructed so as to be chimeric or partially or fully human, so as to reduce or eliminate the adverse immunological consequences resulting from administering to an animal an antibody that has been produced in, or has sequences from, other species.

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that a bacteria containing such a variant may be implemented in compositions and methods. Consequently, a protein need not be isolated.

An antibody or preferably an immunological portion of an antibody, can be chemically conjugated to, or expressed as, a fusion protein with other proteins. For purposes of this specification and the accompanying claims, all such fused proteins are included in the definition of antibodies or an immunological portion of an antibody.

Embodiments provide antibodies and antibody-like molecules against EpCAM, polypeptides and peptides that are linked to at least one agent to form an antibody conjugate or payload. In order to increase the efficacy of antibody molecules as diagnostic or therapeutic agents, it is conventional to link or covalently bind or complex at least one desired molecule or moiety. Such a molecule or moiety may be, but is not limited to, at least one effector or reporter molecule. Effector molecules comprise molecules having a desired activity, e.g., cytotoxic activity. Non-limiting examples of effector molecules that have been attached to antibodies include toxins, therapeutic enzymes, antibiotics, radio-labeled nucleotides and the like. By contrast, a reporter molecule is defined as any moiety that may be detected using an assay. Non-limiting examples of reporter molecules that have been conjugated to antibodies include enzymes, radiolabels, haptens, fluorescent labels, phosphorescent molecules, chemiluminescent molecules, chromophores, luminescent molecules, photoaffinity molecules, colored particles or ligands, such as biotin.

Several methods are known in the art for the attachment or conjugation of an antibody to its conjugate moiety. Some attachment methods involve the use of a metal chelate complex employing, for example, an organic chelating agent such as a diethylenetriaminepentaacetic acid anhydride (DTPA); ethylenetriaminetetraacetic acid; N-chloro-p-toluenesulfonamide; and/or tetrachloro-3-6?-diphenylglycouril-3 attached to the antibody. Monoclonal antibodies may also be reacted with an enzyme in the presence of a coupling agent such as glutaraldehyde or periodate. Conjugates with fluorescein markers are prepared in the presence of these coupling agents or by reaction with an isothiocyanate.

The conjugation of the radionuclide to the antibodies or fragments of the invention can be made using any conventional techniques such as the use of a linker between the antibody and the radioisotope. Preferably, the radioimmunoconjugate has a specific activity of from about 0.5 to about 15 mCi/mg, depending on the radionuclide, and may be administered via an intravenous or other route.

IV. Diagnostic Imaging of Diseases

Certain aspects of the present invention can be used to diagnose and/or image a disease or disorder associated with EpCAM expression, for example, prostate cancer. In this regard, an antibody or antibody fragment can be detectably labeled through the use of radioisotopes, affinity labels (e.g., biotin, avidin, etc.), fluorescent labels, paramagnetic atoms, etc. The detection of foci of such detectably labeled antibodies or antibody fragments might be indicative of a site of tumor development. In a preferred embodiment, this technique is done in a non-invasive manner through the use of magnetic imaging, fluorography, PET, etc. Such a diagnostic test may be employed in monitoring the success of treatment of diseases, where presence or absence of EpCAM-positive cells is a relevant indicator. Such imaging may also be employed during surgical resection of lymph nodes comprising metastatic disease to guide said surgical resection.

Visualization and quantification of MAb biodistribution using PET requires a suitable positron-emitting radionuclide. $^{89}$Zr ($t_{1/2}$=78.4 h), $^{124}$I ($t_{1/2}$=100.3 h), $^{64}$Cu ($t_{1/2}$=12.7 h), $^{86}$Y ($t_{1/2}$=14.7 h), and $^{76}$Br ($t_{1/2}$=16.2 h) are well suited for imaging of intact MAbs.

Where clinical application of a diagnostic composition containing an inhibitory antibody is undertaken, it will generally be beneficial to prepare a pharmaceutical composition appropriate for the intended application. In certain embodiments, pharmaceutical compositions may comprise, for example, at least about 0.1% of an active compound. In other embodiments, an active compound may comprise between about 2% to about 75% of the weight of the unit, or between about 25% to about 60%, for example, and any range derivable therein.

The pharmaceutical compositions of the present invention are advantageously administered in the form of injectable compositions either as liquid solutions or suspensions; solid forms suitable for solution in, or suspension in, liquid prior to injection may also be prepared. These preparations also may be emulsified.

The phrases "pharmaceutical or pharmacologically acceptable" refers to molecular entities and compositions that do not produce an adverse, allergic, or other untoward reaction when administered to an animal, such as a human, as appropriate. The preparation of a pharmaceutical composition comprising an antibody or additional active ingredient will be known to those of skill in the art in light of the present disclosure. Moreover, for animal (e.g., human) administration, it will be understood that preparations should meet sterility, pyrogenicity, general safety, and purity standards as required by FDA Office of Biological Standards.

As used herein, "pharmaceutically acceptable carrier" includes any and all aqueous solvents (e.g., water, alcoholic/aqueous solutions, saline solutions, parenteral vehicles, such as sodium chloride, Ringer's dextrose, etc.), non-aqueous solvents (e.g., propylene glycol, polyethylene glycol, vegetable oil, and injectable organic esters, such as ethyloleate), dispersion media, coatings, surfactants, antioxidants, preservatives (e.g., antibacterial or antifungal agents, anti-oxidants, chelating agents, and inert gases), isotonic agents, absorption delaying agents, salts, drugs, drug stabilizers, gels, binders, excipients, disintegration agents, lubricants, sweetening agents, flavoring agents, dyes, fluid and nutrient replenishers, such like materials and combinations thereof, as would be known to one of ordinary skill in the art. The pH and exact concentration of the various components in a pharmaceutical composition are adjusted according to well-known parameters. A pharmaceutically acceptable carrier is particularly formulated for administration to a human, although in certain embodiments it may be desirable to use a pharmaceutically acceptable carrier that is formulated for administration to a non-human animal but that would not be acceptable (e.g., due to governmental regulations) for administration to a human. Except insofar as any conventional carrier is incompatible with the active ingredient, its use in the therapeutic or pharmaceutical compositions is contemplated.

The term "unit dose" or "dosage" refers to physically discrete units suitable for use in a subject, each unit containing a predetermined quantity of the diagnositc composition calculated to produce the desired responses discussed above in association with its administration, i.e., the appropriate route and treatment regimen. The quantity to be administered, both according to number of treatments and unit dose, depends on the effect desired. The actual dosage amount of a composition of the present invention administered to a patient or subject can be determined by physical and physiological factors, such as body weight, the age, health, and sex of the subject, the type of disease being imaged, the extent of disease penetration, previous or concurrent therapeutic interventions, idiopathy of the patient, the route of administration, and the potency, stability, and toxicity of the particular therapeutic substance. For example, a dose may also comprise from about 1 µg/kg/body weight to about 1000 mg/kg/body weight (this such range includes intervening doses) or more per administration, and any range derivable therein. In non-limiting examples of a derivable range from the numbers listed herein, a range of about 5 µg/kg/body weight to about 100 mg/kg/body weight, about 5 µg/kg/body weight to about 500 mg/kg/body weight, etc., can be administered. The practitioner responsible for administration will, in any event, determine the concentration of active ingredient(s) in a composition and appropriate dose(s) for the individual subject.

The active compounds can be formulated for parenteral administration, e.g., formulated for injection via the intravenous, intramuscular, sub-cutaneous, or even intraperitoneal routes. Typically, such compositions can be prepared as either liquid solutions or suspensions; solid forms suitable for use to prepare solutions or suspensions upon the addition of a liquid prior to injection can also be prepared; and, the preparations can also be emulsified.

The pharmaceutical forms suitable for injectable use include sterile aqueous solutions or dispersions; formulations including sesame oil, peanut oil, or aqueous propylene glycol; and sterile powders for the extemporaneous preparation of sterile injectable solutions or dispersions. In all cases the form must be sterile and must be fluid to the extent that it may be easily injected. It also should be stable under the conditions of manufacture and storage and must be preserved against the contaminating action of microorganisms, such as bacteria and fungi.

The proteinaceous compositions may be formulated into a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

A pharmaceutical composition can include a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion, and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

V. Kits

In various aspects of the invention, a kit is envisioned containing diagnostic agents and/or other therapeutic and delivery agents. In some embodiments, the present invention contemplates a kit for preparing and/or administering a diagnostic agent of the invention. The kit may comprise one or more sealed vials containing any of the pharmaceutical compositions of the present invention. The kit may include, for example, at least one EpCAM antibody as well as reagents to prepare, formulate, and/or administer the components of the invention or perform one or more steps of the inventive methods. In some embodiments, the kit may also comprise a suitable container, which is a container that will not react with components of the kit, such as an eppendorf tube, an assay plate, a syringe, a bottle, or a tube. The container may be made from sterilizable materials such as plastic or glass.

The kit may further include an instruction sheet that outlines the procedural steps of the methods set forth herein, and will follow substantially the same procedures as described herein or are known to those of ordinary skill in the art. The instruction information may be in a computer readable media containing machine-readable instructions that, when executed using a computer, cause the display of a real or virtual procedure of delivering a pharmaceutically effective amount of a diagnostic agent.

VI. EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1—Materials and Methods

Monoclonal Antibody Panel Generation.

Commercially available mouse $IgG_{2b}$ monoclonal Ab (mAb) 9601, specific for human EpCAM, was purchased from R & D Systems (Minneapolis, Minn.) and maintained at −20° C. prior to labeling. To generate in-house anti-EpCAM mAbs, two separate immunization strategies were pursued: BALB/c mice were immunized with either recombinant human (rhu) EpCAM/Fc (960-EP, R&D Systems, Minneapolis, Minn.) or MCF7 cells (HTB-22™, ATCC, Manassas, Va.), a human breast adenocarcinoma line that expresses EpCAM (Prang et al., 2005; Munz et al., 2010). EpCAM/Fc was administered using standard methods as previously described (Pinkston et al., 2011). For whole-cell immunization, MCF7 cells were grown in GIBCO® Dulbecco's Minimal Essential Medium (DMEM) (Invitrogen Corporation, Carlsbad, Calif.) with 10% fetal bovine serum (FBS) to 80%-100% confluency in T75 flasks, detached with Trypsin-ethylenediaminetetraacetic acid (EDTA) (Cellgro, Manassas, Va.), washed in phosphate buffered saline (PBS), pH 7.4, and injected intraperitoneally (ip) at $10^7$ cells per mouse every ten days for five injections. Mouse splenocytes were collected and fused with SP2/0 mouse myeloma cells (Pinkston et al., 2011). MAbs from parental wells were evaluated for binding specificity to rhuEpCAM/Fc via an enzyme-linked immunosorbent assay (ELISA) followed by kinetic screening to rank order high affinity clones using surface plasmon resonance (SPR) (Canziani et al., 2004).

Competitive Binding Assays.

To compare relative binding sites of the inventor's mAb panel, a competitive binding strategy was used to separate the inventor's panel of mAbs into groups with competing and non-competing epitope binding sites. Briefly, a horseradish peroxidase (HRP) labeling kit (Zymed Laboratories, San Francisco, Calif.) was used to HRP-label in-house generated mAbs or commercial mAb 9601. RhuEpCAM/Fc was coated on Microlon® 600 (Greiner Bio-One, Frickenhausen, Germany), 96-well, high-binding plates in PBS at 0.5 µg/ml and 4° C. overnight. After blocking with PBS containing 0.02% Tween-20 and 5% Non-Fat Dry Milk for 1 h and a subsequent wash with PBS, 0.02% Tween (PBST), each selected mAb from the inventor's panel was added to the plate at 2 µg/ml and incubated for 30 min at room temperature (RT). This was followed by the addition of HRP-conjugated mAb at 0.2 µg/ml and incubation for 30 min at RT. Ability of HRP-conjugated mAb to bind rhuEpCAM/Fc was detected via reaction with 3,3',5,5'-tetramethylbenzidine (TMB) substrate (Sigma-Aldrich, St. Louis, Mo.) and measurement of OD 450 nm, using the manufacturer's protocol. Binding of HRP-labeled mAb demonstrated that epitopes were available for binding, while absence of binding by HRP-labeled mAb indicated competitive epitope binding by the primary mAb.

Preparation of Fab Fragments.

Purified mouse $IgG_1$, in-house mAbs 7 and 153, were digested with immobilized Ficin, Kit 44980 (Pierce, Rockford, Ill.), according to the manufacture's protocol. Commercial mAb 9601, $IgG_{2b}$, was digested with immobilized Papain, Kit 44985 (Pierce). Briefly, purified IgG was dialyzed overnight and buffer exchanged with provided digestion buffer(s) without Cysteine-HCl. After a digestion period of 3-4 h, samples were applied to the provided protein A column. The pass-through material containing fragment antigen-binding (Fab) regions was dialyzed against PBS and retained for enrichment via size exclusion chromatography. A GE ÄKTA Explorer (GE Healthcare, Piscataway, N.J.) fast protein liquid chromatography (FPLC) system coupled with a Superdex 200 HR 10/30 FPLC column (GE Healthcare) pre-equilibrated with PBS was utilized to separate the Fab from undigested IgG and F(ab')2. Purity was then assessed by sodium dodecyl sulfate-polyacrylamide gel electrophoresis (SDS-PAGE).

Surface Plasmon Resonance Assessment of Affinity Constant, KD.

In order to discriminate between monovalent and multivalent interactions on quantitative SPR measurements of KD, the binding affinities of the Fab fragments of mAbs were measured using SPR and a Biacore T100 instrument (GE Healthcare). Two flow cells of a CM5 chip were coated with goat anti-human IgG (Fc-specific) (Jackson ImmunoResearch) to approximately 8000 resonance units (RU) with an NHS/EDC Amine Coupling Kit BR-1000-50 (GE Healthcare). All measurements were made at 25° C. using HBS-EP+(10 mM HEPES, 150 mM NaCl, 3 mM EDTA, 0.05% v/v Tween 20, pH 7.4) as running buffer. EpCAM/Fc ligand (R&D Systems) was diluted in HBS-EP+ to 0.5 µg/ml and applied to the coated chip surface. Fab fragments were then tested at five different molar concentrations starting at 50 nM after performing a two-fold dilution series. Flow cells were regenerated with 100 mM phosphoric acid. All samples were applied in duplicate.

Confirmation of MAb Whole-Cell Binding Activity.

PC3 cells (human prostate adenocarcinoma line, CRL1435™, ATCC, Manassas, Va.), grown to 80%-100% confluency in DMEM with 10% FBS, were treated with Trypsin-EDTA and resuspended in PBS containing 2% bovine serum albumin (BSA). One million cells per well were labeled with 5 μg/ml of mAb in a 200-μl volume and incubated on ice for 20 min. After washing with PBS-BSA, phycoerythrin (PE)-conjugated donkey F(ab')2 anti-mouse IgG (Jackson ImmunoResearch, West Grove, Pa.) at 5 μg per sample was added for an additional 20-min incubation. Cells were washed again with PBS-BSA and fixed in 2% paraformaldehyde prior to analyzing (10,000 events) on a BD FACSCalibur Flow Cytometer (BD Biosciences, San Jose, Calif.). Analyses of mean fluorescence intensities (MFI) were performed using WinMDI2.9 software.

Production of MAbs for Animal Model.

One-liter cultures of hybridomas producing selected mAbs were grown in GIBCO® DMEM high glucose media (Invitrogen Corp.) supplemented with 2% FBS for 10 days. Supernatants were centrifuged, filtered (0.2 μm), and purified on a Protein G column (GE Healthcare) per the manufacturer's instructions. Samples were dialyzed against PBS, filtered (0.2 μm), and stored at 4° C. until use.

Testing Species Cross-Reactivity of MAbs.

To determine whether mAbs specific for human EpCAM cross-react with murine EpCAM, the human cell line MCF7 (as described above) and 4T1 cells (mouse mammary carcinoma, CRL2539™, ATCC) were used. Hybridoma cells were grown and mAbs purified as above-described. Rat anti-mouse EpCAM, mAb G8.8 (Developmental Studies Hybridoma Bank, University of Iowa, Iowa City, Iowa) was utilized as a positive control for detection of EpCAM on the surface of 4T1 cells. Following incubation (20 min, on ice) with mAb, cells were washed with PBS-BSA and either DyLIGHT-488 conjugated donkey anti-rat IgG (Jackson ImmunoResearch) or PE-conjugated donkey F(ab') 2 antimouse IgG (Jackson ImmunoResearch) was added at 5 μg per sample and incubated for an additional 20 min for detecting cells bound by rat anti-mouse or mouse antihuman EpCAM mAb, respectively. Cells were washed again with PBS-BSA and fixed in 2% paraformaldehyde prior to analyzing (10,000 events) on a BD FACSCalibur Flow Cytometer (BD Biosciences) using WinMDI2.9 software.

Preparation of Dual-Labeled MAbs.

MAbs were dual-labeled with DOTA chelator and IRDye 800CW, purified, and the number of chelates and NIR dye molecules conjugated per mAb was determined according to procedures described previously (Hall et al., 2011; Meares et al., 1984). Radiolabeling of mAb-conjugates was performed by adding 37 MBq (1 mCi) of $^{64}CuCl_2$ (Radiological Sciences, Washington University Medical School, St. Louis, Mo.) to 100 μg of mAb-conjugate in 0.1 M NaOAc at pH 6.0, followed by incubation at 40° C. for 1 h. The reactions were purified with spin columns as described above and analyzed by radio-thin layer chromatography (TLC) and radio-high-performance liquid chromatography (HPLC).

Determination of Contrast Agent Biological Activity.

NIR flow cytometry was utilized to measure biological activity of the mAb-conjugates prior to use in animals. Human PCa cells (PC3 cell line, ATCC, Manassas, Va.), which overexpress EpCAM (Poczatek et al., 1999), were incubated ($1\times10^6$) with fluorophore-labeled anti-EpCAM specific or isotype control mAb (1 μg) in 200 μl PBS, pH 7.4, at 37° C. with 5% $CO_2$ for 50 min in the dark. A commercial $IgG_{2b}$ isotype control mAb (BD Pharmingen, San Diego, Calif.) and an in-house generated $IgG_1$ isotype control mAb were used in each assay to test for nonspecific binding. After centrifugation at 350×g for 5 min at RT, supernatants were discarded and cells were washed with PBS. As a positive control, IRDye-labeled secondary Ab, goat anti-mouse IgG (LI-COR), was then added to reactions containing cells incubated with unlabeled, commercial mAb 9601. As a negative control for secondary Ab staining, the secondary Ab was also added to cells without primary Ab. Following incubation for 40 min with secondary Ab or PBS, cells were centrifuged as above-described, resuspended in 500 μl PBS, and placed on ice. Analysis immediately followed using a customized BD FACSAria™ II with NIR wavelength excitation and emission detection capability (BD Biosciences San Diego, Calif.). The percentage (%) of cells bound or stained by fluorophore-labeled Ab as well as the median fluorescence intensity (MFI) of the cells in each reaction was recorded. The means and standard deviations (SD) were calculated from three experiments for each mAb tested.

Animal Model.

A DsRed gene-reporter mouse model of PCa LN metastasis was utilized as previously described (17). In brief, 6-8 week-old, male Nu/Nu mice (Charles River, Wilmington, Mass.) were housed and maintained in compliance with protocols approved by the Animal Welfare Committee at the University of Texas Health Science Center at Houston, and with the Association for Assessment and Accreditation of Laboratory Animal Care. PC3 cells (ATCC), which were transfected with p-DsRedExpress-N1 (Clontech Laboratories, Inc., Mountain View, Calif.) and sorted as previously described (Hall et al., 2011), were orthotopically implanted ($1\times10^6$ cells) in the dorsal prostate of each mouse. Non-invasive, longitudinal DsRed fluorescence imaging was performed bi-weekly to monitor tumor growth.

Dual-labeled mAbs (40-50 μg/7.4-12.95 MBq) were administered via the tail vein at 10-12 weeks post-implantation. Within 18-24 hr, non-invasive μPET/CT was performed and immediately followed by in vivo and in situ DsRed reporter-gene and NIRF optical imaging.

PET, NIRF, and DsRed Fluorescence Imaging.

Fluorescence imaging was conducted using custom-built instrumentation described elsewhere (Hall et al., 2011). For DsRed fluorescence imaging, excitation light was supplied at 568 nm by a tunable, air-cooled, argon/krypton laser and emission light (610±5 nm) was collected through a bandpass filter (Andover Corp., Salem, N.H.). NIRF imaging utilized excitation light at 786 nm from a laser diode and emission light was collected through two tandem bandpass filters collecting light at 830±5 nm (Zhu et al., 2010).

Non-invasive μPET/CT was performed using an Inveon System (Siemens Medical Solutions, Knoxville, Tenn.) with multimodality CT and docked PET. Images were analyzed and % ID/g was quantified from PET images using Inveon Research Workplace software (Siemens Medical Solutions). Target-to-background ratios (TBRs) were computed from the % ID/g normalized to normal muscle background. Previously, the inventors showed that LN DsRed fluorescence measured in situ or ex vivo provided comparable or better true-positive LN discrimination than pathology (Hall et al., 2010). Consequently, the inventors used in situ or ex vivo DsRed fluorescence as a measure of ground truth for LN cancer positivity and computed the PET true-positive rate (TPR or sensitivity) versus false-positive rate (FPR, or [1−specificity]) of all LNs examined using ascending TBR as positive cut-off criteria during ROC curve analyses. The area under the curve (AUC) was then computed for each dual-labeled mAb tested.

Data Analyses.

General statistical comparisons of mAbs were made using the Student's t-test, unpaired, or a one-way ANOVA as appropriate with Microsoft® Office Excel 2007 (Microsoft Corporation, Redmond, Wash.) or SigmaPlot® 11 (Systat Software, Inc., San Jose, Calif.) software. For determining similarity of results obtained from different imaging modalities and for performing ROC curve analyses for each mAb, SAS 9.2 (SAS Institute Inc., Cary, N.C.) and SigmaPlot® 11 (Systat Software, Inc.) software were utilized.

Example 2—Results

Anti-EpCAM MAbs Selected by Off Rate Analysis and Competitive Binding.

Figure 2:
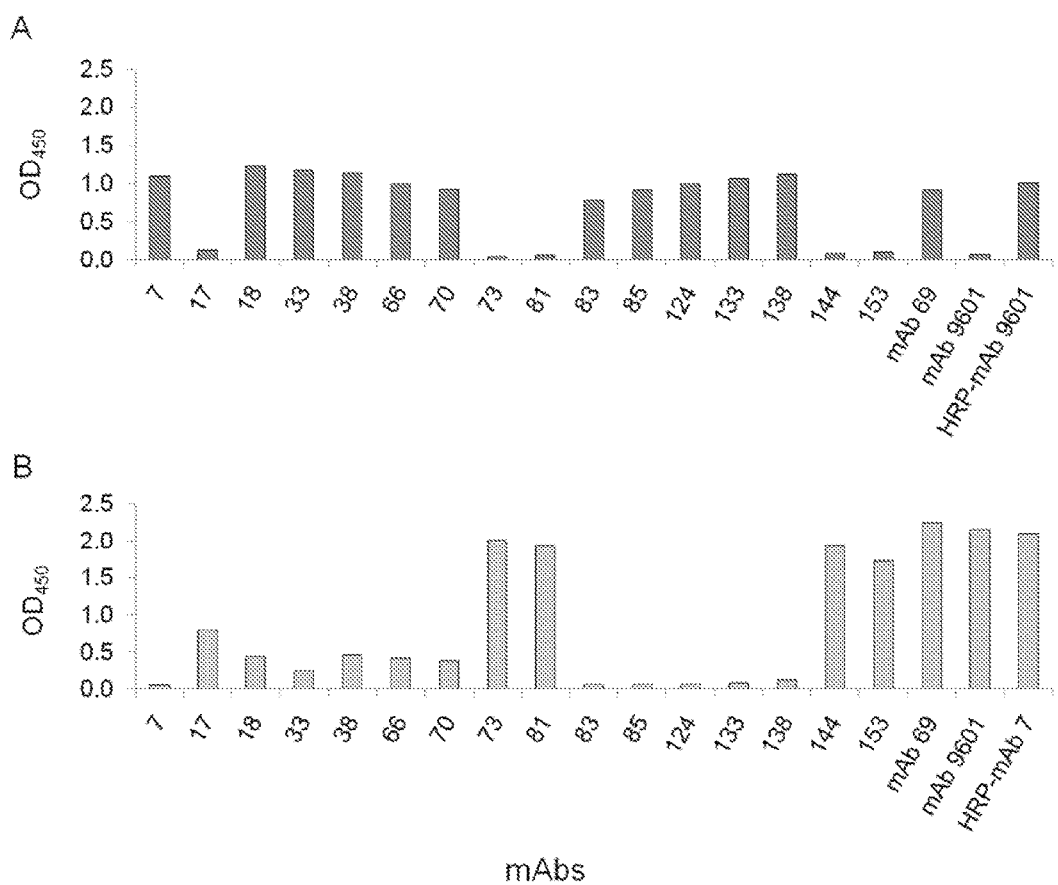
FIG. 2. Competitive binding analysis identified two independent epitopes recognized by the mAb panel. Unlabeled mAb clones (x-axis) bound EpCAM-coated ELISA plates followed by addition of either HRP-labeled anti-EpCAM mAb 9601 or 7. Competing and non-competing epitopes were visualized after washing and addition of HRP substrate. Competing epitopes of mAb 9601 (FIG. 2A) and mAb 7 (FIG. 2B) were those identified which inhibited binding of HRP-labeled mAb whereas non-competing epitopes did not inhibit binding of the labeled mAbs as monitored by HRP signaling (y-axis).

Screening and analyses of single-cell clones from parental wells of hybridoma fusions were performed as previously described (Pinkston et al., 2011; Canziani et al., 2004) and yielded a mAb panel with slower off rates than that of commercial mAb 9601 (FIG. 1). During competitive binding assays, binding of some mAbs, including mAbs 17, 73, 81, 144, and 153, to EpCAM blocked binding by mAb 9601, suggesting shared binding epitopes (FIG. 2A). However, mAbs 7, 18, 33, 38, 66, 70, 83, 85, 124, 133, and 138 did not inhibit mAb 9601 binding, suggesting epitopes that do not overlap or binding sites that do not compete with that of mAb 9601 (FIG. 2B). From subsequent analysis that compared mAb 7 to the mAb panel, the inventors found that mAbs that do not have overlapping epitope binding with mAb 9601, have an overlapping footprint with mAb 7. Thus, the mAb panel could be categorized into two unique groups with specificity for two separate, non-overlapping epitopes on the EpCAM protein. MAbs from each group, mAbs 153 and 7, were chosen for further evaluation. The VH and VL sequences, including the corresponding CDR sequences, for mAb 153 and mAb 7 are shown in Table 1.

0.54, and 2.3 nM for mAbs 9601, 153, and 7 Fab fragments, respectively. These affinity constants translated to a 28- and 7-fold increase in affinity of mAbs 153 and 7 above mAb 9601, respectively.

MAb Whole-Cell Binding Activity.

Figure 3:
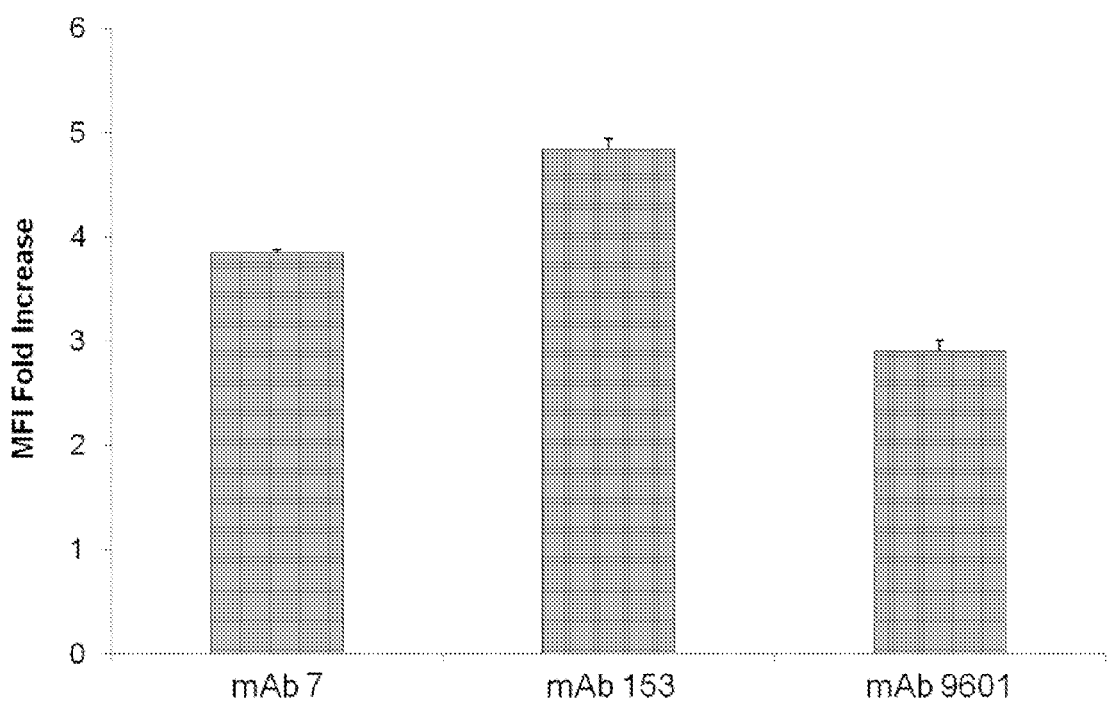
FIG. 3. Selected candidate mAb binding to native EpCAM expression on PC3 cells compared to that of commercial mAb 9601 via flow cytometry. Anti-EpCAM mAb 7, 153, or 9601 was incubated with PC3 cells followed by detection with PE-labeled secondary antibody. The geometric mean fluorescence intensity (MFI) of the cell population was determined by analysis of 10,000 cells using a BD FACSCalibur Flow Cytometer. The fold increase in MFI for cells incubated with each mAb is shown relative to the MFI of cells incubated with only PE-labeled secondary antibody.

As seen with mAb 9601, both mAbs 7 and 153 effectively bound PC3 cells as demonstrated by specific binding during flow cytometry (FIG. 3). An MFI fold increase of 3.9, 4.8, and 2.9 was found for cells bound by mAbs 7, 153, and 9601, respectively, relative to the MFI of cells stained with PE-conjugated secondary antibody alone. This result provides evidence that, in addition to recognizing recombinantly-expressed EpCAM/Fc, these in-house generated mAbs recognize native EpCAM on the cell surface.

Species Cross-Reactivity of MAbs Tested by Whole-Cell Binding.

Figure 7:
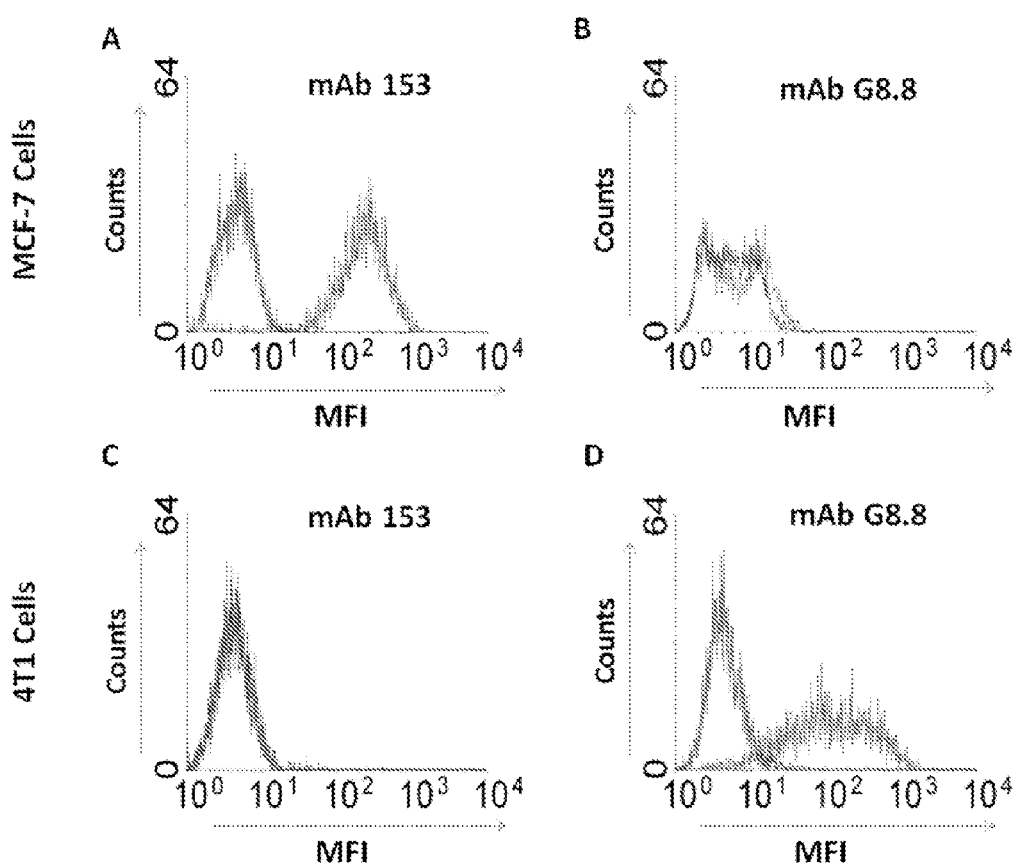
FIG. 7. Analysis of mAb binding to human and mouse carcinoma cells. Anti-EpCAM mAb 153 or G8.8 was incubated with either human MCF7 or mouse 4T1 cells. The mouse anti-human EpCAM mAb 153 and rat anti-mouse mAb G8.8 were detected with species-specific secondary antibodies, PE-labeled anti-mouse IgG, and DyLIGHT 488-labeled anti-rat IgG, respectively. The geometric mean fluorescence intensity (MFI) was determined with a BD FACSCalibur Flow Cytometer using WinMDI2.9 software.

The generated panel of anti-human EpCAM mAbs bound only the human cells and did not bind to the mouse 4T1 cells at detectable levels (see FIGS. 7A and C for results from mAb 153, which are representative of those from the entire mAb panel). Conversely, rat anti-mouse EpCAM mAb G8.8 demonstrated binding to the 4T1 cells, but not to human MCF7 cells (FIGS. 7B and D).

Contrast Agent Characterization.

DOTA conjugation to the mAbs occurred at varying levels for each reaction and ranged from 3.0-4.6 DOTA molecules per mAb, while conjugation of IRDye 800CW to the mAbs resulted in D/P ratios ranging from 2.1-3.4 (Table 2).

TABLE 1

VH and VL CDR Sequences for mAbs 153 and 7

| | Heavy Chain Sequence | | | Light Chain Sequence | | |
|---|---|---|---|---|---|---|
| mAb | CDR1 Amino acid sequence | CDR2 | CDR3 | CDR1 Amino acid sequence | CDR2 | CDR3 |
| 153 | SYWIN (SEQ ID NO: 1) | GDIYPGSGN SHYNEKFKS (SEQ ID NO: 2) | NYYGSSPF PMDY (SEQ ID NO: 3) | KSSQSLLN SGNQKNYLT (SEQ ID NO: 4) | WASTRES (SEQ ID NO: 5) | QNDYTYPLT (SEQ ID NO: 6) |
| | QVQLQQSGAELVKPGTSVKLSCKASG YNFTSYWINWVKLRPGQGLEWIGDIY PGSGNSHYNEKFKSKATLTVDTSSST AYMQLSSLASGDSALYYCARNYYGSS PFPMDYWGQGTSVTVSS (SEQ ID NO: 7) | | | DIVMTQSPSSLIVTAGEKVTMSCKSSQ SLLNSGNQKNYLTWYQQKPGQPPKLLI YWASTRESGVPDRFTGSGSGTDFTLTL NSAQAEDLAVYYCQNDYTYPLTFGAGT KLEIK (SEQ ID NO: 8) | | |
| 7 | GYNMN (SEQ ID NO: 9) | GNIDPYNGG SGFDQKFKG (SEQ ID NO: 10) | EYGSNFDY (SEQ ID NO: 11) | RASQDIGTYLN (SEQ ID NO: 12) | YTSRLHS (SEQ ID NO: 13) | QQGNTLPWT (SEQ ID NO: 14) |
| | QVQLQQSGPELEKPGGSVKISCKASG YSFTGYNMNWVKQSNGKSLEWIGNID PYNGGSGFDQKFKGKATLTVDTSSST AYMHLKSLTSEDSAVYYCAREYGSNF DYWGQGTTLTVSS (SEQ ID NO: 15) | | | DIQMTQSTSSLSASLGDRVTISCRASQDIGTYLN WYQQQADGTFKLLIYYTSRLHSGIPSRFSGSGSG TDFSLTISNLGQEDIATYFCQQGNTLPWTFGGGT KLEIK (SEQ ID NO: 16) | | |

SPR Assessment of Anti-EpCAM MAbs 7 and 153 Fab Fragments.

Fab fragments of mAb 153 demonstrated a slower $K_d$ or "off" rate than that of mAb 7, which in turn was slower than that of mAb 9601 Fab fragment, a trend consistent with SPR analysis of dissociation avidity of captured IgG antibody using the bivalent EpCAM/Fc as the analyte (Table 2). In addition, both mAb 153 and 7 Fab fragments demonstrated significantly faster "on" rates ($K_a$) than that of mAb 9601. The equilibrium affinity constant ($K_D$) was found to be 15.4, Although radiolabeling reactions were performed identically, radiochemical yields were impacted by the amount of DOTA conjugated and were determined to be 60%-80%. Radiochemical purities were greater than 90% for the mAb 9601-conjugate and greater than 95% for all other agents with typical specific activities of 0.185-0.259 MBq (5-7 µCi) per µg protein.

Figure 4:
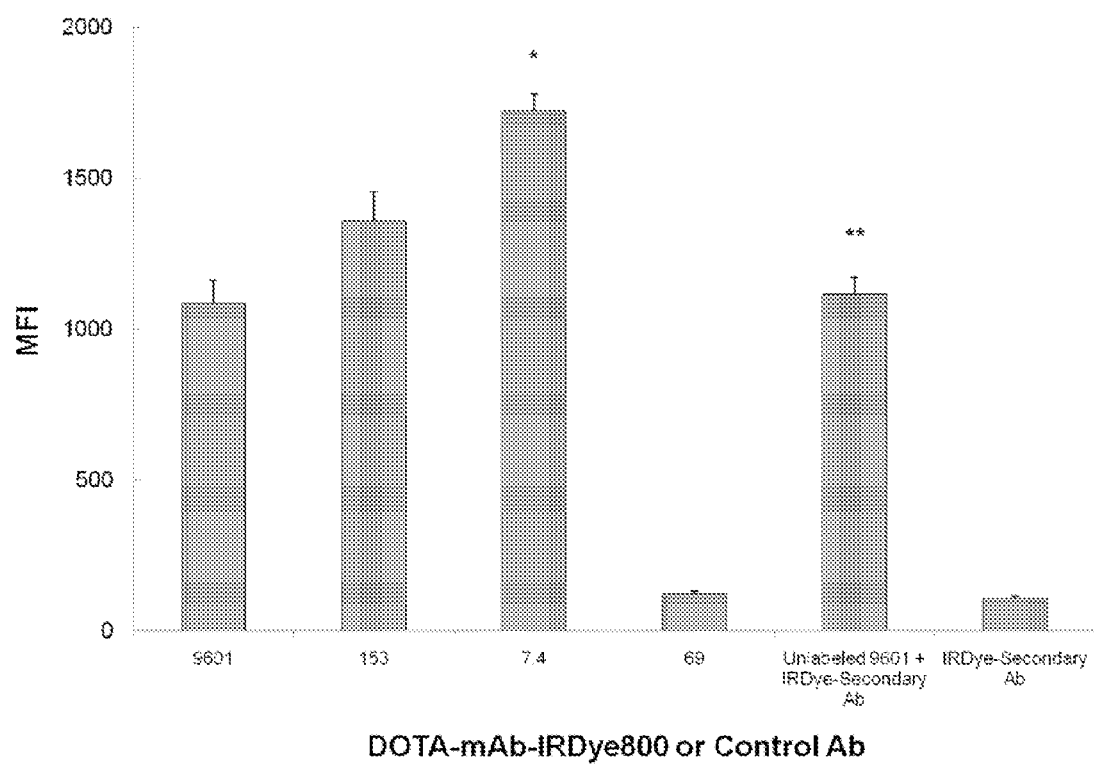
FIG. 4. Median fluorescence intensity (MFI) of PC3 cells bound by IRDye-labeled antibody (Ab), as determined by near-infrared (NIR) flow cytometry. After incubation with conjugated mAb 9601, 153, 7, or 69, or assay control Ab, PC3 cells were analyzed using a customized BD FACS AriaII. *P<0.05 for mAbs 7 and 153 versus mAb 9601, and for mAb 7 versus mAb 153. **P<0.05 for unlabeled mAb 9601 followed by IRDye-labeled secondary Ab versus IRDye-labeled secondary Ab alone. No significant difference (P>0.05) was found for unlabeled mAb 9601 followed by IRDye-labeled secondary Ab versus conjugated mAb 9601.

From NIR flow cytometry, the inventors found that PC3 cells stained by IRDye-labeled mAbs 7 and 153 had significantly higher MFIs (1722.0±57.4 and 1359.3±94.8 MFI units, respectively) relative to PC3 cells bound by conjugated mAb 9601 (1087.0±74.0 MFI units), while the MFI for mAb 7 was also significantly higher than that for mAb 153 (P<0.05, FIG. 4). IgG$_1$ isotype control mAb 69 had a significantly lower MFI (124.7±7.3 MFI units) relative to mAbs 7 and 153 (P<0.05), as did commercial IgG$_{2b}$ isotype control mAb (149±6.0 MFI units) relative to mAb 9601. The biological activity, measured as the mean percentage of PC3 cells stained, of conjugated mAb 7 (86.4±1.8%) was significantly greater than that of IRDye-labeled mAb 9601 (79.5±0.8%) (P<0.05, Table 2). While the biological activity of mAb 153 (81.8±1.5%) was also higher than that of mAb 9601, the difference was not found to be significant. The percentage of cells stained by IgG$_1$ isotype control mAb 69 (3.2±0.3%) was significantly low relative to mAbs 7 and 153, as was the percentage of cells stained by commercial IgG$_{2b}$ isotype control mAb (0.7±0.1%) relative to mAb 9601 (P<0.05). The MFI (1116.5±54.5 MFI units) as well as the percentage (80.2±5.5%) of cells bound by unlabeled mAb 9601 followed by incubation with IRDye-labeled secondary Ab was not significantly different from that of cells stained directly by conjugated mAb 9601, demonstrating that the NIR fluorophore label did not significantly hinder mAb binding to its target on PC3 cells.

Similarly, in situ NIRF imaging of the same mouse (FIGS. 5E and H) demonstrated that the same cancer-positive tissue could be detected from specifically bound, dual-labeled mAb. The tissues are also shown in white light images (FIGS. 5F and I). Radiotracer and NIRF signals were also detected in the liver, kidneys, and bladder, which is not uncommon for the whole-mAb imaging agent. For all LNs examined by DsRed fluorescence and NIRF imaging, the correlation between the two imaging modalities was between 0.8 and 1.0 for all mAbs tested.

Quantitative PET Image Analyses.

Table 3 lists the mean TBR of % ID/g for DsRed-positive LNs in PCa-positive mice and the AUC for each dual-labeled imaging agent tested. While the percentage of DsRed-positive (i.e. cancer-positive) LNs found in each group of mice was similar (range, 10%-14%), the mean TBRs for DsRed-positive LNs in mice administered dual-labeled mAbs 7 (5.79±3.3% ID/g) and 153 (3.77±0.9% ID/g) were significantly higher (P<0.05) than the mean TBR for DsRed-positive LNs in mice given the dual-labeled isotype control mAb 69 (1.79±0.9% ID/g). No significant difference was found between TBRs for in-house mAbs 7 and 153; however, the mean TBR found for mAb 9601 (3.68±3.2% ID/g) was significantly lower than that for mAb 7 (P<0.05).

TABLE 2

Characterization of Imaging Conjugates.

| mAb | Fab Association Constant ($k_a$) [M$^{-1}$ s$^{-1}$] | Fab Dissociation Constant ($k_d$) [s$^{-1}$] | Fab Equilibrium Constant ($K_D = k_d/k_a$) [nM] | No. of DOTA/ Protein (SD) | No. of IRDye800/ Protein (SD) | Biological Activity, % (SD) |
|---|---|---|---|---|---|---|
| 9601 | 2.6 × 10$^5$ | 4.0 × 10$^{-3}$ | 15.1 | 3.0 (1.0) | 2.3 (0.5) | 79.5 (0.8) |
| 153 | 2.2 × 10$^5$ | 1.2 × 10$^{-4}$ | 0.53 | 4.6 (1.1) | 2.1 (0.5) | 81.8 (1.5) |
| 7 | 4.3 × 10$^5$ | 9.9 × 10$^{-4}$ | 2.3 | 5.1 | 2.3 | 86.4 (1.8) * |
| 69 | NA† | NA | NA | 4.2 (2.6) | 3.4 (0.4) | 3.2 (0.3) ** |

\* P < 0.05 for mAb 7 versus 9601 and 153.
\*\* P < 0.05 for IgG$_1$ isotype control mAb 69 versus mAb 7 and 153; and for commercial IgG$_{2b}$ isotype control (0.7 ± 0.1%) versus mAb 9601.
†NA, not applicable as mAb 69 is an isotype control targeting pili.

Multimodal Imaging.

Figure 8:
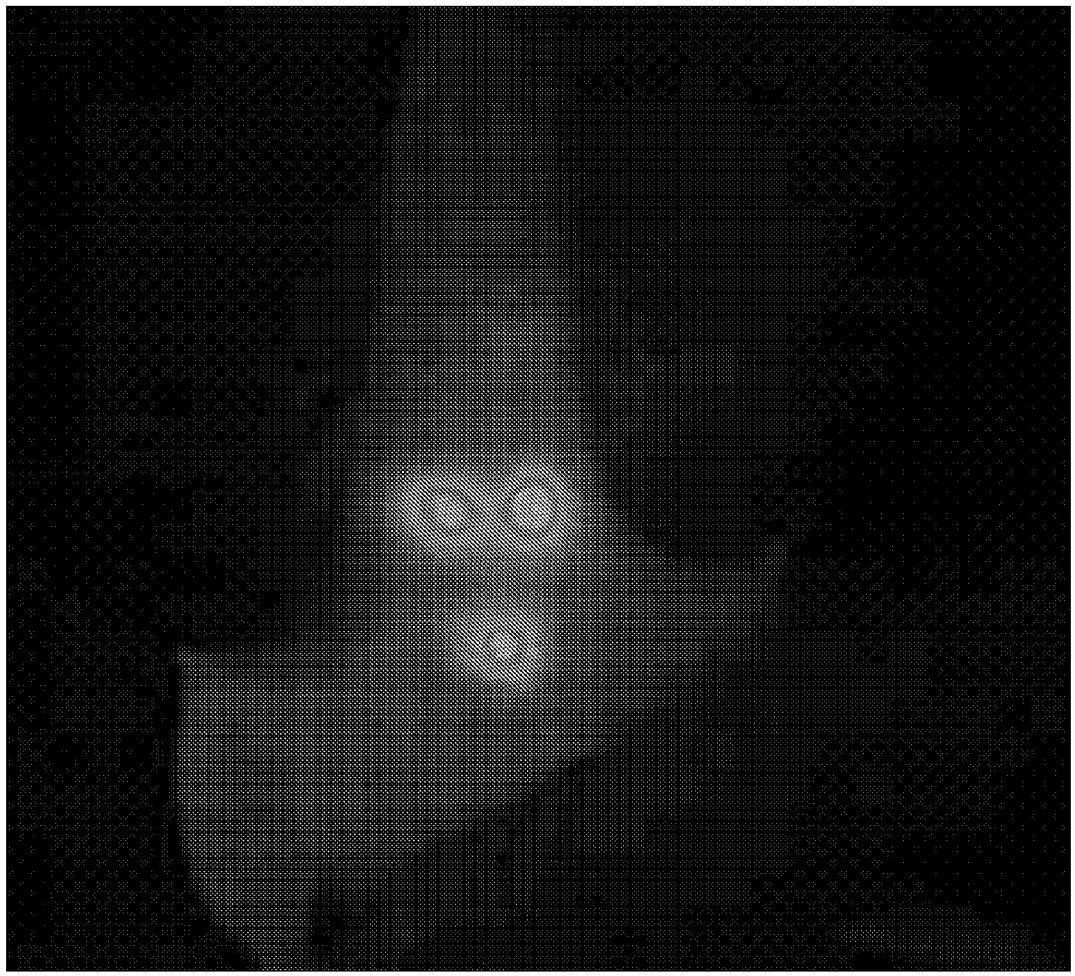
FIG. 8. DsRed fluorescence imaging video of animal LN staging. Longitudinal DsRed fluorescence imaging was performed in vivo at two-week intervals post-implantation of DsRed-expressing PC3 cells to monitor primary tumor growth and detect metastatic LNs if present. LN staging could be performed successfully in vivo for some mice, with or without holding the skin slightly taut. Metastases usually involved the lumbar LNs (as shown with holding), and sometimes medial iliac, renal, sciatic, inguinal, or popliteal LNs.

Non-invasive, DsRed fluorescence imaging of each mouse at two-week intervals allowed for monitoring of primary prostate tumors and detection of LN involvement in some animals. While primary tumors and some metastatic LNs could be easily visualized, it was necessary to hold the abdominal skin taut on some mice for LN staging (see FIG. 8). By week 10-12 post-implantation, metastases usually involved the lumbar LNs, and sometimes also medial iliac, renal, sciatic, inguinal, or popliteal LNs.

Figure 5:
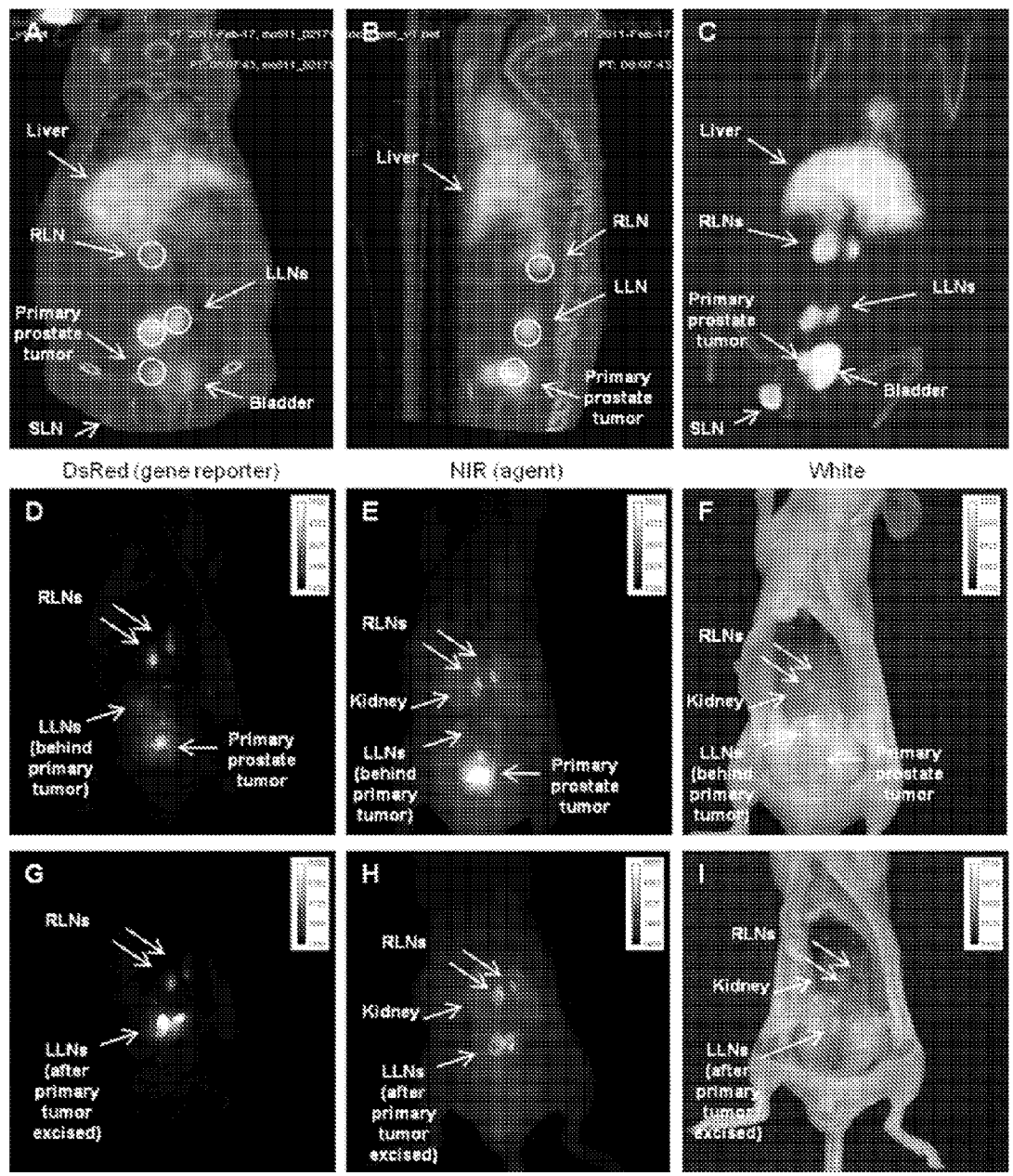
FIG. 5. Non-invasive PET/CT and invasive DsRed and near-infrared (NIR) fluorescence images of a representative mouse having a primary prostate tumor and metastatic lymph nodes (LNs). Following dual-labeled mAb administration, coronal (FIG. 5A) and sagittal (FIG. 5B) views from PET/CT show radiotracer signal in the prostate region and several LNs. Regions of interest (ROI, white circles) were drawn around cancer-positive tissue using Inveon Research Workplace (IRW) software. The % ID/g was calculated for each ROI (including background muscle tissue) using IRW. The 3-D view from PET/CT (FIG. 5C) demonstrates better tissue delineation relative to single-slice 2-D views, including delineating primary tumor from bladder, metastatic renal LNs (RLNs) from kidneys and liver (where agent is cleared), and a metastatic sciatic LN (SLN). In situ DsRed fluorescence images (FIGS. 5D and G) of a ventral view from the same animal confirm the presence of a primary prostate tumor and cancer-positive lumbar LNs (LLNs) and RLNs via PC3 cell DsRed reporter-gene expression. The same cancer-positive tissues were detected via in situ NIR fluorescence imaging (FIGS. 5E and H) due to specific binding by dual-labeled mAb (agent). Anatomical location of tissue is depicted by corresponding white light photographs (FIGS. 5F and I) taken during in situ imaging.

From non-invasive μPET/CT, radiotracer signal from primary prostatic tumors and LNs bound by dual-labeled mAb was detected. FIG. 5 shows coronal (FIG. 5A), sagittal (FIG. 5B), and 3-D (FIG. 5C) views from μPET/CT of a representative mouse in which the prostate, lumbar, and renal LNs, and one sciatic LN were PET-positive. In situ DsRed gene-reporter imaging (FIGS. 5D and G) demonstrated the presence of PC3 cells in the same tissues, confirming a primary tumor and LN metastases. DsRed fluorescence in this animal's right sciatic LN was observed during in vivo imaging of the dorsal side as well as ex vivo imaging.

Figure 6:
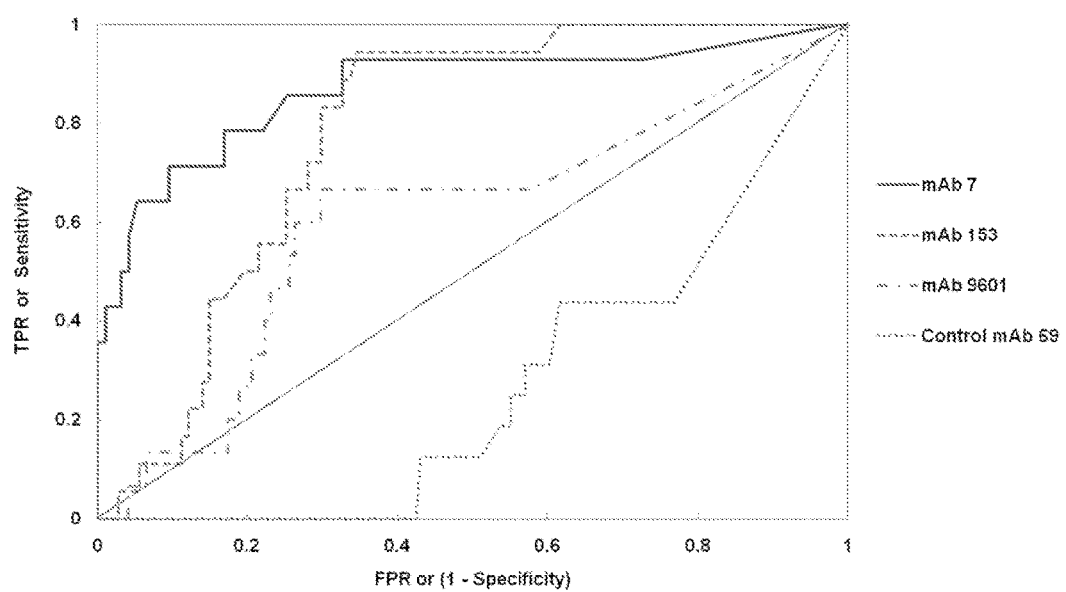
FIG. 6. Receiver operating characteristic (ROC) curve analyses of TBR of % ID/g measured from PET/CT of LNs in mice given dual-labeled mAb 153, 7, 9601, or 69 (with $^{64}$Cu-DOTA and IRDye800). DsRed fluorescence from the gene reporter was considered the true-positive indicator of cancer-positive cells in LNs. The true-positive rate (TPR) or sensitivity was plotted versus false-positive rate (FPR or [1−specificity]) for each mAb using ascending positive cut-off values, or criteria, that defined positive PET results. The ROC curve and area under the curve (AUC) for each mAb is demonstrated. While a perfect classification is defined as TPR=1.0 and FPR=0, mAbs 7 and 153 each demonstrated a significantly higher AUC or concordance rate (86.8% and 78.0%, respectively) relative to the 50% random chance line of no discrimination (dashed line). No significant differences were found between the concordance rates for mAbs 9601 or 69 relative to the 50% nondiscriminatory line. mAb 69 targets another molecule besides EpCAM and thus has imaging performance below the diagonal change line.

FIG. 6 shows the ROC curve generated for each dual-labeled mAb tested. The AUC for dual-labeled mAbs 7 (86.8%) and 153 (78.0%) were both significantly greater than the 50% nondiscriminatory line (P<0.05), whereas the AUC for mAb 9601 (60.7%) was not significantly different from a 50/50 random guess (Table 3). The AUC (27%) for isotype control mAb 69, which is specific for pili expression in E. faecalis (Gao et al., 2010), was less than 50%. Given that a perfect classification in ROC analysis is defined as TPR=1.0 and FPR=0, mAbs 7 and 153 each demonstrated better classification or "concordance" between μPET/CT and DsRed-reporter gene signals, and overall higher sensitivity relative to commercial mAb 9601 and control mAb 69. Using optimal TBR cut-off values that maximized the functions of the ROC curve generated for each mAb (Table 3), the inventors found that the corresponding sensitivities for in-house mAbs 153 (94%) and 7 (93%) were substantially greater than the sensitivity found for commercial mAb 9601 (67%). The specificities were found to be similar for the three mAb-conjugates.

TABLE 3

Quantitative PET Image Analyses using DsRed-positive LNs as the True-positive Indicator of LN Metastases.

| mAb | No. of Mice Tested | No. of LNs Examined (% DsRed-positive) | Mean TBR of % ID/g* (SD) | AUC† (%) | Sensitivity (%) | Specificity (%) | Optimal TBR Cut-off (% ID/g) |
|---|---|---|---|---|---|---|---|
| 9601 | 10 | 136 (11) | 3.68 (3.2) | 60.7 | 66.7 | 70.3 | ≥2.81 |
| 153 | 9 | 125 (14) | 3.77 (0.9) ‡ | 78.0§ | 94.4 | 65.4 | ≥2.67 |
| 7 | 10 | 107 (13) | 5.79 (3.3) ‡ | 86.8§ | 92.9 | 66.7 | ≥2.44 |
| 69 | 15 | 167 (10) | 1.79 (0.9) | 27.0 | 43.8 | 38.4 | ≥2.48 |

*Mean TBR of % ID/g (SD) for DsRed-positive lymph nodes in prostate cancer-positive mice.
†AUC, area under curve from receiver operating characteristic (ROC) curve analysis (curves are shown in FIG. 6).
‡ $P < 0.05$ for mAbs 7 and 153 versus mAb 69, and for mAb 7 versus mAb 9601. No significant difference was found between mAbs 7 and 153.
§$P < 0.05$ for mAbs 7 and 153 versus AUC of 50% (line of nondiscrimination).

Comparison to Anti-EpCAM mAB VU-1D9.

Figure 9:
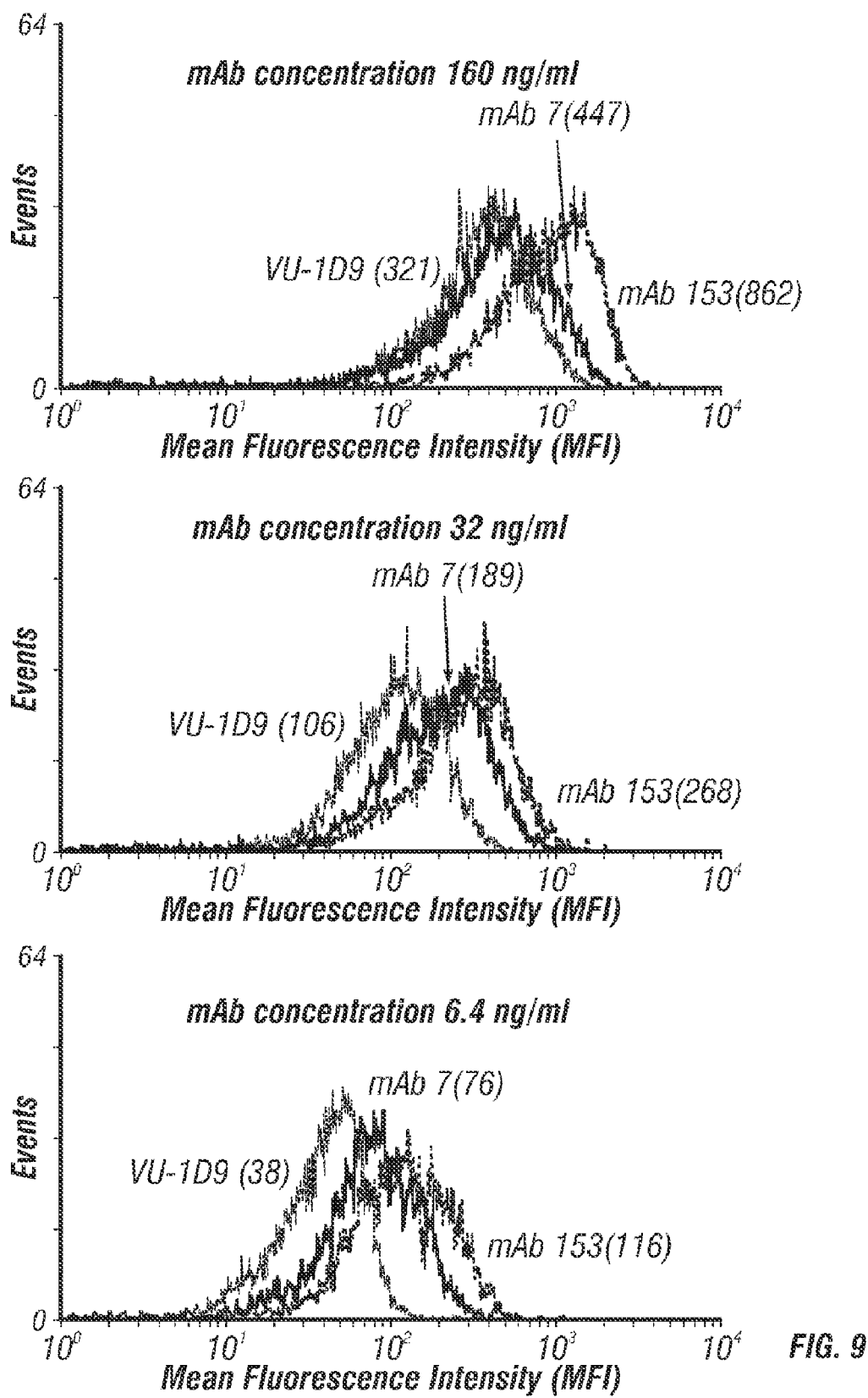
FIG. 9. Comparison of in house generated mAbs 7 and 153 to Veridex mAb VU-1D9 by flow cytometry. Using decreasing levels of primary antibody for labeling breast cancer cell line MCF7 followed by a fluorescently labeled secondary antibody, 10,000 cells from each population were analyzed by flow cytometry and MFI reported. Upon decreasing the level of primary antibody, in house mAbs 7 and 153 demonstrated improved ability to recognize and label surface expressed EpCAM on MCF7s. Numbers in parentheses represent MFI.

It has also been shown that these mAbs also compare favorably to Veridex's anti-EpCAM mAb VU-1D9, a high affinity mAb that functions in rare cell detection and isolation on the Veridex FDA approved platform to quantify circulating tumor cells (CTCs) in patient blood samples. Improving the anti-EpCAM antibody reagent in this application should improve the ability to detect rare cancer cell events in patient blood samples. By using limiting dilutions of mAb 7, 153, or VU-1D9 followed by a fluorescently conjugated secondary anti-mouse antibody to label human breast cancer cell line MCF-7 cells, the inventors demonstrated improved sensitivity of mAb 7 and 153 over that of Veridex VU-1D9 (FIG. 9).

Conversion to scFvs.

These lead antibody candidates were also converted into scFvs using techniques previously described (Krebber et al., 1997). Comparison of these scFvs to the parental mAbs demonstrated that: (i) the scFvs retained affinity to natively displayed EpCAM as monitored through labeling studies of the prostate cancer cell line PC3 (FIG. 10) and (ii) the affinities of the scFvs as measured by Biacore were comparable to the measurements of Fab fragments physically cleaved from the full length mAbs 7 and 153 (FIG. 10) (Hall et al., 2012). The conversion of the lead mAbs to scFvs with comparable affinities to the parent antibody binding domain (i) demonstrates the capability of accurately measuring and retaining affinity while converting to different antibody formats and (ii) the conversion to the scFv antibody format allows for the expression of the antibody binding domain in *Escherichia coli*, required for affinity maturation of this antibody using display technologies.

Figure 10A:
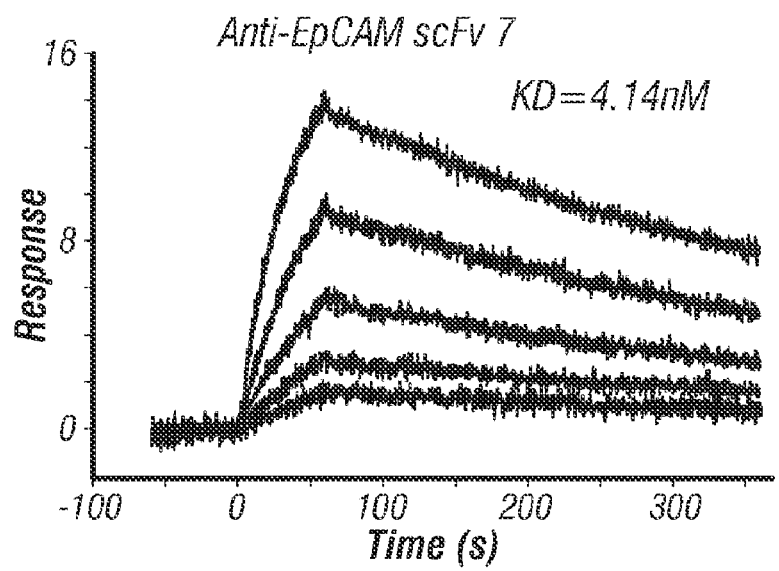
FIG. 10. Evaluation of scFv anti-EpCAM binding. Population of human prostate cancer cell line PC3 cells labeled with scFv 7 or scFv 153 detected with fluorophore conjugated secondary antibody and analyzed by flow cytometry (FIG. 10C), demonstrated mean fluorescent intensities (MFI) of 380 and 1164 compared to secondary control MFI of 10. Affinity of anti-EpCAM scFvs was determined by Biacore kinetic analysis. scFv 7 and scFv 153 were measured to have affinities of 4.14 nM and 0.21 nM, respectively (FIGS. 10A and B). This compares similarly to the affinity determination of Fab fragments produced via cleavage of parent mAbs 7 and 153, which demonstrated affinities of 2.3 nM and 0.54 nM, respectively. Slight differences may be attributed to accuracy in measuring active concentrations of Fab vs scFv prior to kinetic evaluation.
Figure 10B:
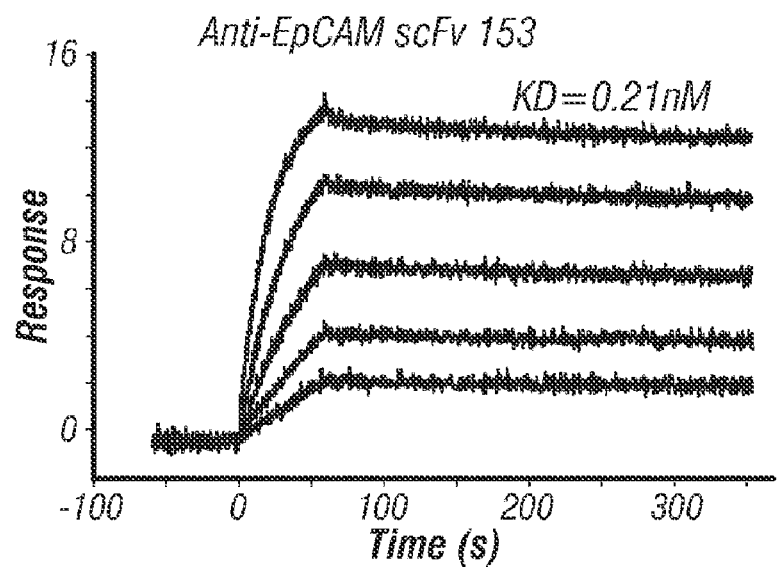
Figure 10C:
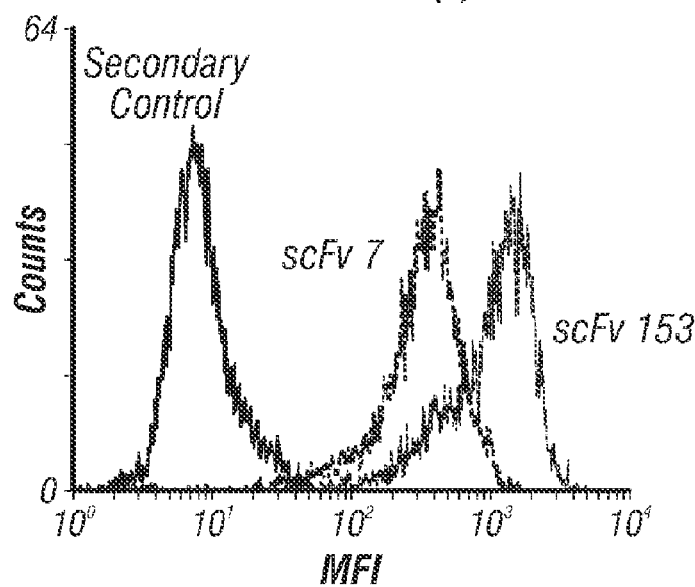
Figure 11:
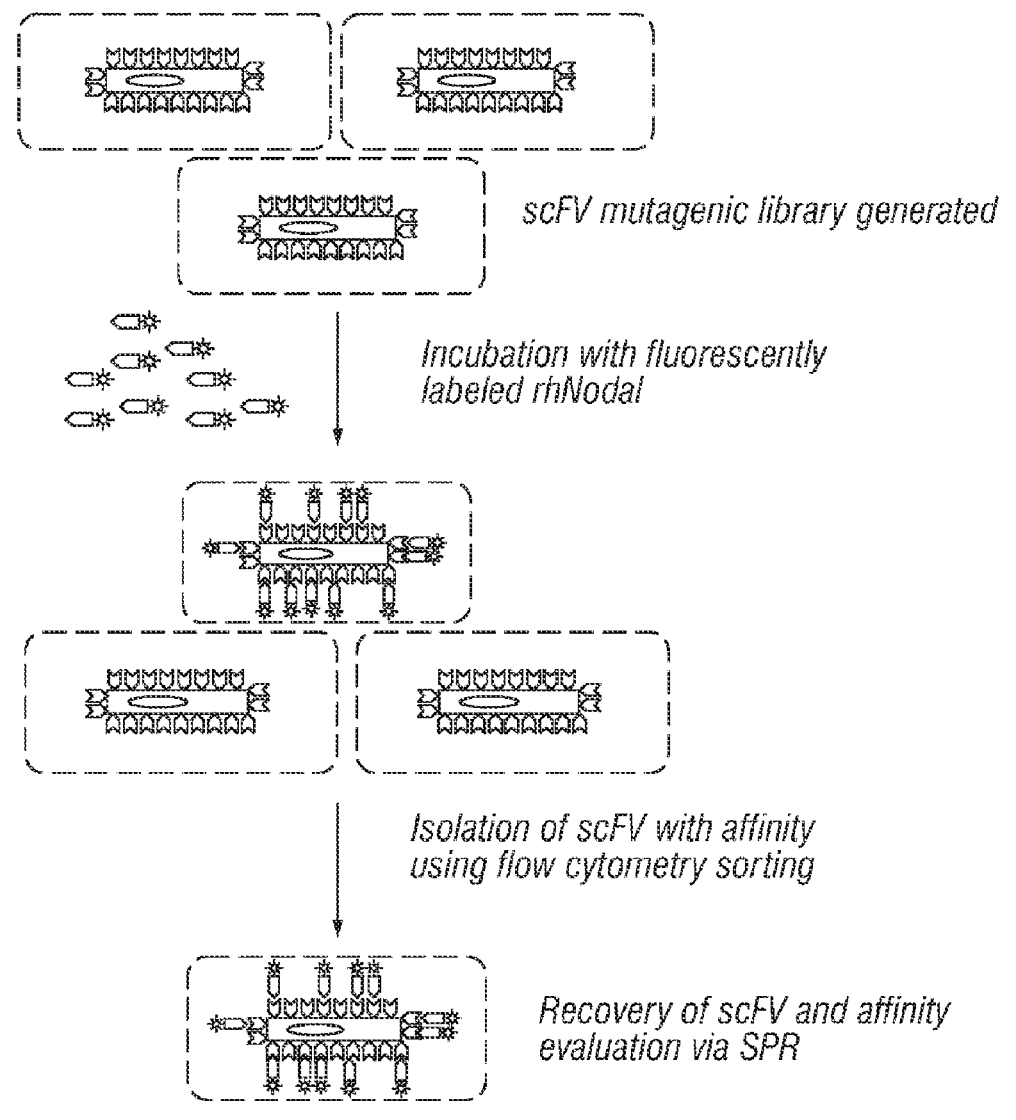
Figure 12:
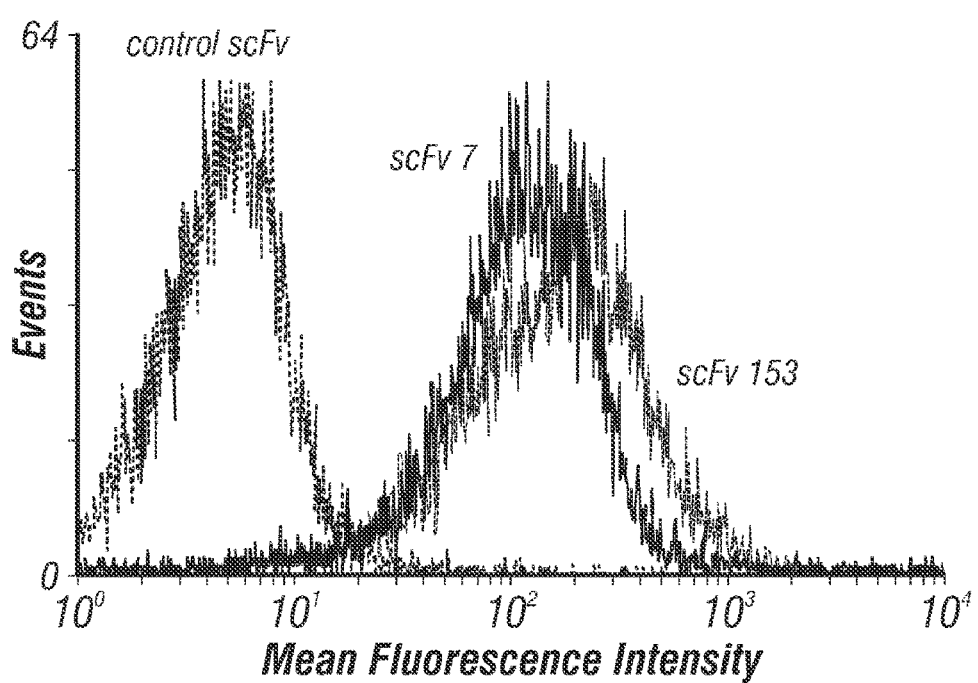
FIG. 12. Evaluation of population of 10,000 E. coli cells displaying anti-EpCAM scfv 7 and 153 via the APEx platform can be specifically labeled with EpCAM-Fc followed by detection with fluorescently conjugated secondary antibody with MFIs of 170 and 248, respectively. This is compared to an E. coli population expressing scFv with no affinity to EpCAM as a control, labeled under these conditions with a MFI of only 13. Affinity of scFv correlates with scFv affinity to EpCAM, with resolution dependent on stringency of the wash steps on E. coli prior to evaluation.

Cells expressing the scFv library will be incubated with the EpCAM-Fc antigen (R&D Systems) and subsequently washed to remove low affinity interactions. Those *E. coli* cells expressing scFv that retain EpCAM-Fc represent mutants with higher affinity to EpCAM. Detection of EpCAM-Fc levels retained on the *E. coli* surface is achieved with a fluorescently conjugated secondary anti-Fc antibody and cells are isolated via flow cytometry (FIG. 11). Selected scFvs will be expressed and their affinity determined by Biacore as and compared to parental scFv affinities (FIG. 10). To demonstrate feasibility of this system, the inventors have completed initial experiments in which both anti-EpCAM scFvs 7 and 153 have been cloned into the pAPEx1 vector for *E. coli* display. Incubation with EpCAM-Fc followed by detection with fluorescently conjugated anti-Fc demonstrated specific labeling of the *E. coli* population, as compared to *E. coli* cells expressing a control scFv with no affinity to EpCAM or labeling cells with secondary control alone (FIG. 12).

Conversion of Lead Anti-EpCAM scFvs to IgG and Confirmation of Affinity Improvements.

To demonstrate the activity of affinity matured antibodies head to head with commercially available anti-EpCAM mAbs including Veridex anti-EpCAM VU-1D9 among others, the scFvs must be returned to full length IgG molecules. For IgG conversion of selected scFvs, the variable regions of the scFv will be PCR amplified. DNA encoding each of the heavy and light chain variable regions will be cloned in frame with DNA encoding the mAb constant regions. Expression will be driven by the CMV promoter in 293 Freestyle cells as previously described (An et al., 2009). Secreted mAbs will then be purified from medium using protein A/G affinity chromatography. The concentration of purified mAbs will be determined by OD280 nm and the purity by SDS-PAGE. Biacore analysis will confirm affinity improvement of IgG as described (Hall et al., 2012).

Affinity Maturation of Lead Anti-EpCAM Antibody Candidates 7 and 153.

Affinity maturation of the antigen binding domain of mAb 7 and 153 will be used to achieve strikingly higher sensitivity with these antibodies for both improved diagnostic imaging performance and improvements in CTC cell detection and isolation. For affinity maturation, scFv 7 and scFv 153 DNA sequences that have been identified will be utilized as template to generate mutagenic libraries as previously described (Fromant et al. 1995). Each sequence resulting from mutagenesis that bears a unique set of mutations is then cloned into the pAPEx1 vector for protein expression and display of the library on the *E. coli* inner membrane via a new lipoprotein A (N1 pA) fusion as previously described (Harvey et al., 2004; Harvey et al., 2006).

Evaluation of Affinity Matured mAbs for Cancer Detection.

Through limiting dilution labeling of EpCAM on prostate and breast cancer cell lines PC3 and MCF7 and subsequent flow cytometry detection, the inventors can compare the Veridex antibody VU-1D9, the parent antibodies 7 and 153, and the affinity matured candidates to monitor for improved sensitivity of cell labeling and detection. This will be done essentially as described above (FIG. 9) in the parental mAb studies. Confirmation of affinity improvements and improved sensitivity of these mAbs to epithelial carcinoma cell lines will significantly improve their utility in cancer detection for both cancer/metastatic imaging and CTC identification/isolation applications.

Example 3—Discussion

Sentinel LN dissection (SLND) has been standard-of-care in breast cancer staging and recently, has been under investigation for staging PCa (Holl et al., 2009; Janetschek et al., 2007). It is also notable that with the advent of improved systemic treatment, recent studies have shown that breast cancer patients with limited sentinel LN metastases have gained no benefit from extensive LN dissection (Giuliano et al., 2011). Earlier detection of PCa using PSA testing and PLND may continue to decrease mortality rates due to PCa, but may also inherently increase the risk for overtreatment in low-risk PCa patients (Jemal et al., 2010), especially with the advent of new pharmacologic therapies against PCa. A molecularly targeted imaging agent that offers both benefits of noninvasive imaging and intraoperative guidance for resection of cancer-positive LNs is needed for more accurate and effective PCa staging as well as staging of other epithelial cancers.

EpCAM, which is overexpressed in >98% of PCa cases (Went et al., 2004; Rao et al., 2005), was identified 30 years ago as a tumor-associated antigen that today is known to be intensely and uniformly expressed on many epithelial carcinomas while being less intensely expressed and less accessible on the basolateral surface of normal epithelia (Benko et al., 2011; Herlyn et al., 1979; Sears et al., 1982; Sears et al., 1984; Stoecklein et al., 2006). When administered therapeutically, anti-EpCAM mAbs with the highest binding affinities are not well tolerated in clinical studies. Instead, anti-EpCAM mAbs with attenuated affinities exhibit less systemic toxicity and have been moderately successful in clinical trials (Munz et al., 2010). Yet, when administered as a diagnostic at sub-therapeutic dosages, the attenuated affinity of anti-EpCAM mAbs could potentially impact imaging sensitivity, thus motivating the inventor's studies to evaluate imaging performance. Furthermore, when full-length, affinity-attenuated mAbs are converted to fragments, their reduced circulation times will not only offer more desirable pharmacokinetics to reduce background imaging signal, but would most likely result in reduced targeting and imaging sensitivity. While others have employed therapeutic mAbs as radio- and fluorescently-labeled diagnostic agents in clinical and preclinical studies, the inventors sought herein to first develop mAbs with the highest affinities and assess imaging performance prior to further modification.

The inventor's SPR-based selection strategy allowed us to identify high-affinity mAbs produced from hybridoma clones for testing in a mouse model of human PCa LN metastases. Imaging analysis was accelerated by the use of a fluorescent DsRed gene reporter as "ground truth" during assessment of LN metastases. Consistent with SPR affinity of the Fab fragment measurements, dual-labeled mAbs 153 and 7 as imaging agents possessed greater sensitivity than mAb 9601 and had a significantly higher AUC than the 50% line of non-discrimination. In contrast, the AUC of mAb 9601 was not statistically greater than the line of random chance. While the TBRs of % ID/gm of cancer-positive LNs imaged using dual-labeled mAbs 153 and 7 were significantly greater than that found using mAb 69, and while the TBR using mAb 7 was significantly greater than that found using mAb 9601, there was no significant difference between the TBRs or AUCs of dual-labeled mAbs 153 and 7, even though their measured Fab fragment affinities were different by four-fold. Because mAbs 153 and 7 possess different epitope binding footprints, the comparison of their imaging performance may not be appropriate relative to the comparison between mAbs 9601 and 153, which do share the same binding epitope on the EpCAM protein. Nonetheless, these results suggest that mAb affinity can dramatically impact imaging performance. The inventors expect that the impact of affinity on imaging performance may be more significant when using Ab fragments since limited target accessibility due to reduced circulation times could restrict imaging sensitivity.

While there are limited reports of quantitative, molecular imaging in animal models of metastatic disease in the literature, there are significant shortcomings associated with studies of Ab-based targeting of human epitopes in mouse models. Because the mAbs used herein possessed low efficiency in targeting homologous mouse EpCAM in vitro, the imaging specificity may be artificially high in these studies. On the contrary, it is also important to note that these quantitative results may have under-predicted specificity due to the fact that the mAbs tested were whole mAb molecules having Fc regions. Nonspecific binding of full mAbs by Fc receptors on immunocompetent cells, such as NK cells, macrophages, dendritic cells, and neutrophils, is inherent in animal models. Reduction of nonspecific binding can be achieved through modification of the Fc region (Strohl et al., 2009) or by developing dual-labeled specific Ab fragments, such as diabodies, or single-chain variable fragments (scFv) to eliminate Fc regions (Olafsen et al., 2010). In addition to being a mechanism for nonspecific binding (Fischman et al., 1990), Fc receptor-mediated interaction with mAb is known to play an important role in reducing mAb clearance (Kosterink et al., 2007), increasing half-life in the blood circulation (Datta-Mannan et al., 2007), and therefore increasing background signal that in turn can reduce imaging contrast. Taken together, these phenomena obviate the need for mAb fragment-based agent development during contrast agent optimization for detection of metastatic LNs in PCa.

Although preclinical NIRF tomography is under development in several laboratories, quantitative optical imaging remains to be validated and was not employed in the study presented herein. Nonetheless, fluorescent DsRed gene-reporter imaging enabled rapid identification of LN metastases and provided ground truth for assessing true- and false-positive rates for evaluation of both PET and NIRF imaging from a single, dual-labeled agent. The limit in the number of cancer cells detected from either μPET or NIRF imaging was not assessed here, but following optimization of mAb fragment-based agent, will be studied from concordance of cytometric analyses of DsRed- and NIRF-positive cells from resected LNs. The inventors nonetheless used established, quantitative μPET/CT imaging to assess the performance of dual-labeled mAb-based agents for detecting human PCa LN metastasis in an orthotopic mouse model. These studies demonstrate that affinity can impact imaging performance as evaluated using ROC analyses.

All of the methods disclosed and claimed herein can be made and executed without undue experimentation in light of the present disclosure. While the compositions and methods of this invention have been described in terms of preferred embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Patent Application Nos. 2002/0172677; 2004/0126828; and 20050214860

U.S. Pat. Nos. 3,817,837; 3,850,752; 3,939,350; 3,996,345; 4,196,265; 4,275,149; 4,277,437; 4,366,241; 4,469,797; 4,472,509; 4,606,855; 4,703,003; 4,742,159; 4,767,720; 4,816,567; 4,867,973; 4,938,948; 4,946,778; 5,021,236; 5,091,513; 5,164,296; 5,196,066; 5,223,409; 5,403,484; 5,420,253; 5,565,332; 5,571,698; 5,627,052; 5,656,434; 5,770,376; 5,789,208; 5,821,337; 5,844,091; 5,858,657; 5,861,155; 5,871,907; 5,969,108; 6,054,297; 6,165,464; 6,365,157; 6,406,867; 6,709,659; 6,709,873; 6,753,407; 6,814,965; 6,849,259; 6,861,572; 6,875,434; 6,881,557; 6,891,024; and 6,946,546.

Hu et al., *Cancer Res.*, 56, 3055-3061, 1996

Liu et al. *Cell Mol. Biol.*, 49(2):209-216, 2003

Marks, et al., *J. Biol. Chem.* 267:16007-16010 1992

Stemmer, *Nature*, vol. 370, p. 389-391, 1994;

Gram et al. *Proc. Natl. Acad. Sci.*, USA, 89:3576-3580, 1992

Barbas et al., *Proc. Natl. Acad. Sci.*, USA, 91:3809-3813, 1994

Schier et cd. *J. Mol. Biol.* 263:551-567, 1996

Shukla-Dave et al., "Detection of prostate cancer with MR spectroscopic imaging: an expanded paradigm incorporating polyamines," *Radiology*. November 2007; 245(2): 499-506.

Berney et al., International Society of Urological Pathology (ISUP) Consensus Conference on Handling and Staging of Radical Prostatectomy Specimens. Working group 4: seminal vesicles and lymph nodes, *Mod Pathol*. January 2011; 24(1):39-47.

Daskivich et al. Overtreatment of men with low-risk prostate cancer and significant comorbidity. *Cancer.* May 15, 2011; 117(10):2058-2066.

Pilepich et al., Surgical staging in carcinoma of the prostate: the RTOG experience. Radiation Therapy Oncology Group. *Prostate.* 1984; 5(5):471-476.

Musch et al., Complications of pelvic lymphadenectomy in 1,380 patients undergoing radical retropubic prostatectomy between 1993 and 2006. *J Urol.* March 2008; 179(3):923-928; discussion 928-929.

Cormier et al., Lymphedema beyond breast cancer: a systematic review and meta-analysis of cancer-related secondary lymphedema. *Cancer.* Jul. 27, 2010.

Spizzo et al. Overexpression of epithelial cell adhesion molecule (Ep-CAM) is an independent prognostic marker for reduced survival of patients with epithelial ovarian cancer. *Gynecol Oncol*. November 2006; 103(2):483-488.

Spizzo et al. High Ep-CAM expression is associated with poor prognosis in node-positive breast cancer. *Breast Cancer Res Treat*. August 2004; 86(3):207-213.

Went et al. Frequent high-level expression of the immunotherapeutic target Ep-CAM in colon, stomach, prostate and lung cancers. *Br J Cancer.* Jan. 16, 2006; 94(1):128-135.

Fong et al. Ep-CAM expression in pancreatic and ampullary carcinomas: frequency and prognostic relevance. *J Clin Pathol*. January 2008; 61(1):31-35.

Baeuerle EpCAM (CD326) finding its role in cancer. *Br J Cancer.* Feb. 12, 2007; 96(3):417-423.

Benko et al., Impact of the EpCAM expression on biochemical recurrence-free survival in clinically localized prostate cancer. *Urol Oncol. Apr.* 20, 2011.

Mukherjee et al. *Identification of EpCAM as a molecular target of prostate cancer stroma. Am J Patha* December 2009; 175(6):2277-2287.

Edge et al., *AJCC Cancer Staging Manual*. Seventh ed. New York, N.Y.: Springer; 2010.

Zellweger et al. Expression patterns of potential therapeutic targets in prostate cancer. *Int J Cancer*. Feb. 10, 2005; 113(4):619-628.

Hall et al. Imaging prostate cancer lymph node metastases with a multimodality contrast agent. *The Prostate.* 2011, DOI: 10.1002/pros.21413.

Prang et al. Cellular and complement-dependent cytotoxicity of Ep-CAM-specific monoclonal antibody MT201 against breast cancer cell lines. *Br J Cancer.* Jan. 31, 2005; 92(2):342-349.

Munz et al. Side-by-side analysis of five clinically tested anti-EpCAM monoclonal antibodies. *Cancer Cell Int.* 2010; 10:44.

Pinkston et al. The Fsr quorum-sensing system of *Enterococcus faecalis* modulates surface display of the collagen-binding MSCRAMM Ace through regulation of gelE. *J Bacteria* September 2011; 193(17):4317-4325.

Canziani et al., Kinetic screening of antibodies from crude hybridoma samples using Biacore. *Anal Biochem. Feb.* 15, 2004; 325(2):301-307.

Meares et al., Conjugation of antibodies with bifunctional chelating agents: isothiocyanate and bromoacetamide reagents, methods of analysis, and subsequent addition of metal ions. *Anal Biochem*. October 1984; 142(1):68-78.

Poczatek et al. Ep-Cam levels in prostatic adenocarcinoma and prostatic intraepithelial neoplasia. *J Urol.* October 1999; 162(4): 1462-1466.

Zhu et al., Reduction of excitation light leakage to improve near-infrared fluorescence imaging for tissue surface and deep tissue imaging. *Med Phys*. November 2010; 37(11): 5961-5970.

Gao et al., *Enterococcus faecalis* rnjB is required for pilin gene expression and biofilm formation. *J Bacteriol*. October 2010; 192(20):5489-5498.

Holl et al., Validation of sentinel lymph node dissection in prostate cancer: experience in more than 2,000 patients. *Eur J Nucl Med Mol Imaging*. September 2009; 36(9): 1377-1382.

Janetschek et al., [Sentinel lymph node dissection for localized prostate cancer]. *Actas Urol Esp*. June 2007; 31(6): 686-692.

Giuliano et al. Axillary dissection vs no axillary dissection in women with invasive breast cancer and sentinel node metastasis: a randomized clinical trial. *JAMA*. 2011; 305 (6):569-575.

Jemal et al., Cancer statistics, 2010. *CA Cancer J Clin.* September-October 2010; 60(5):277-300.

Went et al. Frequent EpCam protein expression in human carcinomas. *Hum Pathol*. January 2004; 35(1):122-128.

Rao et al. Expression of epithelial cell adhesion molecule in carcinoma cells present in blood and primary and metastatic tumors. *Int J Oncol*. July 2005; 27(1):49-57.

Herlyn et al., Colorectal carcinoma-specific antigen: detection by means of monoclonal antibodies. *Proc Natl Acad Sci USA*. March 1979; 76(3): 1438-1442.

Sears et al. Phase-I clinical trial of monoclonal antibody in treatment of gastrointestinal tumours. *Lancet. Apr.* 3, 1982; 1(8275):762-765.

Sears et al., Effects of monoclonal antibody immunotherapy on patients with gastrointestinal adenocarcinoma. *J Biol Response Mod.* 1984; 3(2): 138-150.

Stoecklein et al. Ep-CAM expression in squamous cell carcinoma of the esophagus: a potential therapeutic target and prognostic marker. *BMC Cancer*. 2006; 6:165.

Strohl Optimization of Fc-mediated effector functions of monoclonal antibodies. *Curr Opin Biotechnol*. December 2009; 20(6):685-691.

Olafsen et al., Antibody vectors for imaging. *Semin Nucl Med*. May 2010; 40(3):167-181.

Fischman et al. Localization of Fc and Fab fragments of nonspecific polyclonal IgG at focal sites of inflammation. *J Nucl Med*. July 1990; 31(7):1199-1205.

Kosterink et al. Biodistribution studies of epithelial cell adhesion molecule (EpCAM)-directed monoclonal antibodies in the EpCAM-transgenic mouse tumor model. *J Immunol*. Jul. 15, 2007; 179(2):1362-1368.

Datta-Mannan et al., Monoclonal antibody clearance. Impact of modulating the interaction of IgG with the neonatal Fc receptor. *J Biol Chem*. Jan. 19, 2007; 282(3): 1709-1717.

Hall et al., Imaging Prostate Cancer Lymph Node Metastases with a Multimodality Contrast Agent. Prostate 2011.

Hall et al., Comparison of Mabs Targeting Epithelial Cell Adhesion Molecule for the Detection of Prostate Cancer Lymph Node Metastases with Multimodal Contrast Agents: Quantitative Small-Animal Pet/Ct and Nirf. *J Nucl Med* 2012, 53(9):1427-1437.

Krebber et al., Reliable Cloning of Functional Antibody Variable Domains from Hybridomas and Spleen Cell Repertoires Employing a Reengineered Phage Display System. J Immunol Methods 1997, 201(1):35-55.

Fromant et al., Direct Random Mutagenesis of Gene-Sized DNA Fragments Using Polymerase Chain Reaction. Anal Biochem 1995, 224(1):347-353.

Harvey et al., Anchored Periplasmic Expression, a Versatile Technology for the Isolation of High-Affinity Antibodies from *Escherichia Coli*-Expressed Libraries. Proc Natl Acad Sci USA 2004, 101(25):9193-9198.

Harvey et al., Engineering of Recombinant Antibody Fragments to Methamphetamine by Anchored Periplasmic Expression. J Immunol Methods 2006, 308(1-2):43-52.

An et al: Igg2m4, an Engineered Antibody Isotype with Reduced Fc Function. MAbs 2009, 1(6):572-579.

Wallwiener et al: The Prognostic Impact of Circulating Tumor Cells in Subtypes of Metastatic Breast Cancer. Breast Cancer Res Treat 2013, 137(2):503-510.

Young et al., Circulating Tumor Cells in Lung Cancer. Acta Cytol 2012, 56(6):655-660.

Sun et al., Circulating Stem Cell-Like Epcam(+) Tumor Cells Indicate Poor Prognosis of Hepatocellular Carcinoma after Curative Resection. Hepatology 2012.

What is claimed is:

1. An isolated monoclonal antibody, wherein the antibody specifically binds to a EpCAM polypeptide and comprises:
   (a) a first $V_H$ CDR of the 7 monoclonal antibody (SEQ ID NO: 9);
   (b) a second $V_H$ CDR of the 7 monoclonal antibody (SEQ ID NO: 10);
   (c) a third $V_H$ CDR of the 7 monoclonal antibody (SEQ ID NO: 11);
   (d) a first $V_L$ CDR of the 7 monoclonal antibody (SEQ ID NO: 12);
   (e) a second $V_L$ CDR of the 7 monoclonal antibody (SEQ ID NO: 13); and
   (f) a third $V_L$ CDR of the 7 monoclonal antibody (SEQ ID NO: 14).

2. The antibody of claim 1, wherein the antibody comprises a $V_H$ domain at least about 80% identical to the $V_H$ domain of 7 (SEQ ID NO: 15) and a $V_L$ domain at least about 80% identical to the $V_L$ domain of 7 (SEQ ID NO: 16).

3. The antibody of claim 2, wherein the antibody comprises a $V_H$ domain identical to the $V_H$ domain of 7 (SEQ ID NO: 15) and a $V_L$ domain identical to the $V_L$ domain of 7 (SEQ ID NO: 16).

4. The antibody of claim 1, wherein the antibody has an equilibrium $K_D$ relative to EpCAM of between about 0.1 and 10 nM.

5. The antibody of claim 4, wherein the antibody has an equilibrium $K_D$ relative to EpCAM of less than about 5 nM.

6. The antibody of claim 1, wherein the antibody is the 7 antibody.

7. The antibody of claim 1, wherein the antibody is recombinant.

8. The antibody of claim 1, wherein the antibody is an IgG, IgM, IgA or an antigen binding fragment thereof.

9. The antibody of claim 1, wherein the antibody is a Fab', a F(ab')2, a F(ab')3, a monovalent scFv, or a bivalent scFv.

10. The antibody of claim 1, wherein the antibody is a humanized antibody or de-immunized antibody.

11. The antibody of claim 1, wherein the antibody is conjugated to an imaging agent, a chemotherapeutic agent, a toxin or a radionuclide.

12. The antibody of claim 11, wherein the antibody is conjugated to a fluorophore and a radionuclide.

13. A composition comprising an antibody of claim 1 in a pharmaceutically acceptable carrier.

14. A method of preparing a subject for imaging, comprising administering to the subject an effective amount of an antibody of claim 1, wherein the antibody is conjugated to an imaging agent.

* * * * *